United States Patent
Shin et al.

(10) Patent No.: US 11,717,577 B2
(45) Date of Patent: *Aug. 8, 2023

(54) METHOD FOR PREPARING LONG-ACTING DRUG CONJUGATE THROUGH PREPARATION OF INTERMEDIATE

(71) Applicant: HANMI PHARM. CO., LTD., Hwaseong-si (KR)

(72) Inventors: Cheongbyeol Shin, Hwaseong-si (KR); Dooseo Jang, Hwaseong-si (KR); Ji Hye Moon, Hwaseong-si (KR); Dong Hyun Kim, Hwaseong-si (KR); Ji Eun Lee, Hwaseong-si (KR)

(73) Assignee: HANMI PHARM. CO., LTD., Hwaseong-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 17/627,890

(22) PCT Filed: Jul. 18, 2019

(86) PCT No.: PCT/KR2019/008912
§ 371 (c)(1),
(2) Date: Jan. 18, 2022

(87) PCT Pub. No.: WO2021/010532
PCT Pub. Date: Jan. 21, 2021

(65) Prior Publication Data
US 2022/0257788 A1  Aug. 18, 2022
US 2023/0103271 A2  Mar. 30, 2023

(51) Int. Cl.
*A61K 38/00* (2006.01)
*A61K 47/68* (2017.01)
*A61K 47/60* (2017.01)
*C07K 14/605* (2006.01)

(52) U.S. Cl.
CPC .......... *A61K 47/6811* (2017.08); *A61K 38/00* (2013.01); *A61K 47/60* (2017.08); *C07K 14/605* (2013.01)

(58) Field of Classification Search
CPC ... A61K 47/60; A61K 47/545; C07K 2319/30
See application file for complete search history.

(56) References Cited

U.S. PATENT DOCUMENTS 9,394,546 B2   7/2016  Kim et al.

FOREIGN PATENT DOCUMENTS

| EP | 3 248611 | * 11/2017 |
| JP | 2009-538273 A | 11/2009 |
| JP | 2010-528993 A | 8/2010 |
| JP | 2013-537525 | 10/2013 |
| JP | 2019-515972 | 6/2019 |
| KR | 10-2014-0109342 A | 9/2014 |
| KR | 10-2014-0130711 A | 11/2014 |
| KR | 10-2014-0141358 A | 12/2014 |
| KR | 10-2017-0104409 A | 9/2017 |
| WO | 96/32478 A1 | 10/1996 |
| WO | 97/34631 A1 | 9/1997 |
| WO | 2007/021129 | 2/2007 |
| WO | WO 2011/126997 | * 10/2011 |
| WO | 2017/052329 | 3/2017 |
| WO | 2017/146443 A1 | 8/2017 |
| WO | 2018/147641 A1 | 8/2018 |
| WO | 2019/066609 A1 | 4/2019 |

OTHER PUBLICATIONS

Shiyao Fu, et al., "Dual-Modified Novel Biomimetic Nanocarriers Improve Targeting and Therapeutic Efficacy in Glioma", ACS Applied Materials & Interfaces, 2019, pp. 1841-1854, vol. 11.
"WHO Drug Information", <https://apps.who.int/medicinedocs/documents/s23502en/s23502en.pdf>, 2018, pp. 187-398, vol. 32, No. 2.
Notice of Allowance issued from Korean Patent Application No. 10-2020-7021823 dated Sep. 7, 2021.
International Search Report for PCT/KR2019/008912 dated Apr. 17, 2020 (PCT/ISA/210).

* cited by examiner

*Primary Examiner* — Gyan Chandra
(74) *Attorney, Agent, or Firm* — Sughrue Mion, PLLC

(57) ABSTRACT

Provided is a novel method for preparing a long-acting drug conjugate and a long-acting drug conjugate prepared using the method.

5 Claims, 1 Drawing Sheet

Specification includes a Sequence Listing.

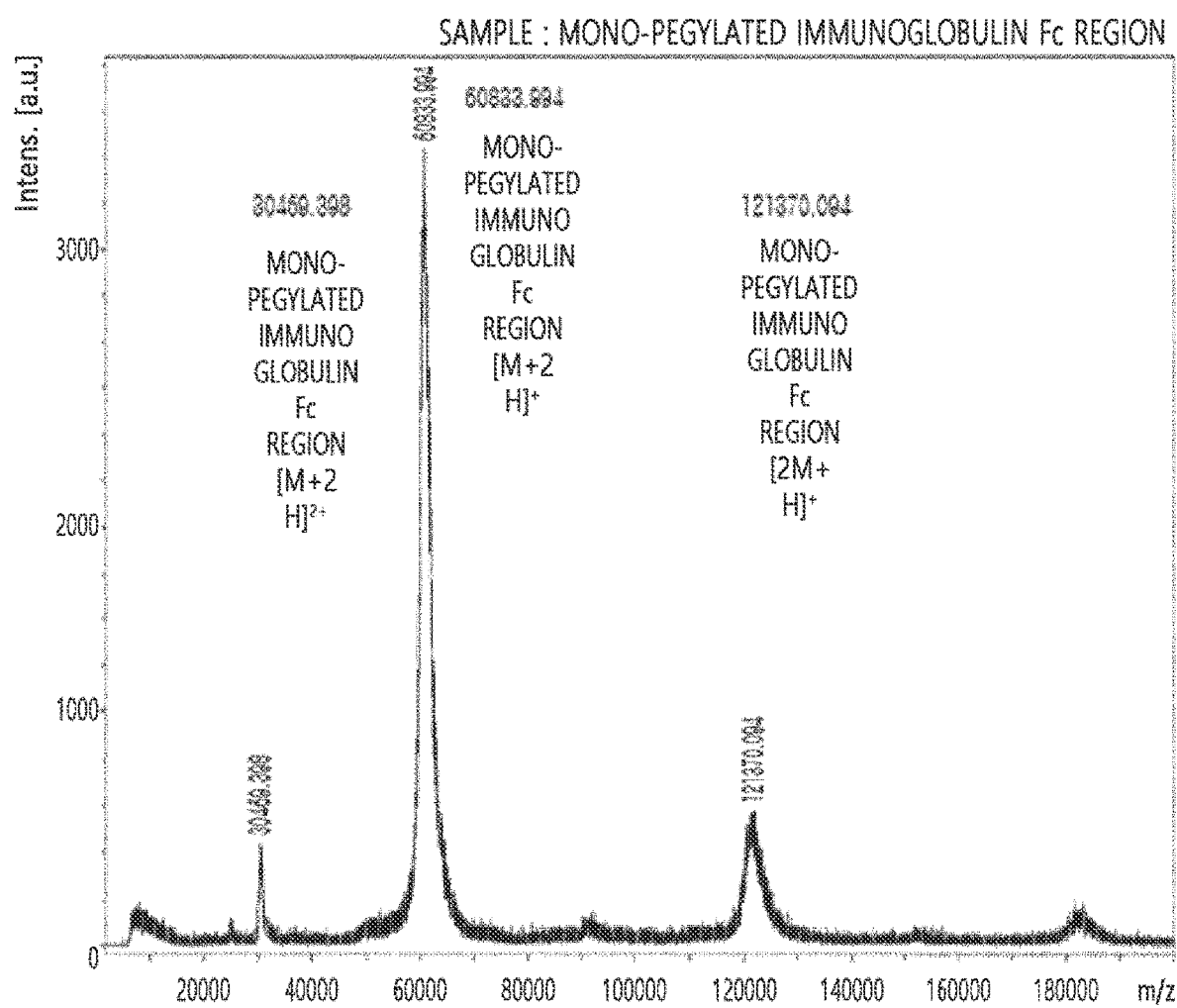

SEQUENCE LISTING

```
<160> NUMBER OF SEQ ID NOS: 28

<210> SEQ ID NO 1
<211> LENGTH: 40
<212> TYPE: PRT
<213> ORGANISM: Artificial Sequence
<220> FEATURE:
<223> OTHER INFORMATION: GLP-1/GIP/Glucagon Triple Agonist analog 1
<220> FEATURE:
<221> NAME/KEY: VARIANT
<222> LOCATION: (2)
<223> OTHER INFORMATION: Xaa = aminoisobutyric acid

<400> SEQUENCE: 1

Tyr Xaa Gln Gly Thr Phe Thr Ser Asp Tyr Ser Lys Tyr Leu Asp Glu
```

```
1               5                   10                  15
Lys Arg Ala Lys Glu Phe Val Gln Trp Leu Leu Asp His His Pro Ser
            20                  25                  30

Ser Gly Gln Pro Pro Ser Cys
        35                  40

<210> SEQ ID NO 2
<211> LENGTH: 39
<212> TYPE: PRT
<213> ORGANISM: Artificial Sequence
<220> FEATURE:
<223> OTHER INFORMATION: GLP-1/GIP/Glucagon Triple Agonist analog 2
<220> FEATURE:
<221> NAME/KEY: VARIANT
<222> LOCATION: (2)
<223> OTHER INFORMATION: Xaa = aminoisobutyric acid

<400> SEQUENCE: 2

Tyr Xaa Gln Gly Thr Phe Thr Ser Asp Tyr Ser Lys Tyr Leu Asp Glu
1               5                   10                  15

Lys Arg Ala Lys Glu Phe Val Gln Trp Leu Leu Asp His His Cys Ser
            20                  25                  30

Ser Gly Gln Pro Pro Pro Ser
        35

<210> SEQ ID NO 3
<211> LENGTH: 40
<212> TYPE: PRT
<213> ORGANISM: Artificial Sequence
<220> FEATURE:
<223> OTHER INFORMATION: GLP-1/GIP/Glucagon Triple Agonist analog 3
<220> FEATURE:
<221> NAME/KEY: VARIANT
<222> LOCATION: (2)
<223> OTHER INFORMATION: Xaa = aminoisobutyric acid

<400> SEQUENCE: 3

His Xaa Gln Gly Thr Phe Thr Ser Asp Tyr Ser Lys Tyr Leu Asp Glu
1               5                   10                  15

Lys Arg Ala Lys Glu Phe Val Gln Trp Leu Leu Asp His His Pro Ser
            20                  25                  30

Ser Gly Gln Pro Pro Pro Ser Cys
        35                  40

<210> SEQ ID NO 4
<211> LENGTH: 30
<212> TYPE: PRT
<213> ORGANISM: Artificial Sequence
<220> FEATURE:
<223> OTHER INFORMATION: Glucagon analog 1
<220> FEATURE:
<221> NAME/KEY: VARIANT
<222> LOCATION: (2)
<223> OTHER INFORMATION: Xaa = aminoisobutyric acid

<400> SEQUENCE: 4

Tyr Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Cys
            20                  25                  30

<210> SEQ ID NO 5
<211> LENGTH: 29
<212> TYPE: PRT
<213> ORGANISM: Artificial Sequence
```

```
<220> FEATURE:
<223> OTHER INFORMATION: Glucagon analog 2
<220> FEATURE:
<221> NAME/KEY: VARIANT
<222> LOCATION: (2)
<223> OTHER INFORMATION: Xaa = aminoisobutyric acid

<400> SEQUENCE: 5

Tyr Xaa Gln Gly Thr Phe Thr Ser Asp Tyr Ser Lys Tyr Leu Asp Glu
1               5                   10                  15

Cys Arg Ala Lys Glu Phe Val Gln Trp Leu Met Asn Thr
            20                  25

<210> SEQ ID NO 6
<211> LENGTH: 30
<212> TYPE: PRT
<213> ORGANISM: Artificial Sequence
<220> FEATURE:
<223> OTHER INFORMATION: Glucagon analog 3
<220> FEATURE:
<221> NAME/KEY: VARIANT
<222> LOCATION: (2)
<223> OTHER INFORMATION: Xaa = aminoisobutyric acid

<400> SEQUENCE: 6

Tyr Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Cys
            20                  25                  30

<210> SEQ ID NO 7
<211> LENGTH: 12
<212> TYPE: PRT
<213> ORGANISM: homo sapiens

<400> SEQUENCE: 7

Glu Ser Lys Tyr Gly Pro Pro Cys Pro Ser Cys Pro
1               5                   10

<210> SEQ ID NO 8
<211> LENGTH: 3
<212> TYPE: PRT
<213> ORGANISM: Artificial Sequence
<220> FEATURE:
<223> OTHER INFORMATION: Variant of hinge region

<400> SEQUENCE: 8

Ser Cys Pro
1

<210> SEQ ID NO 9
<211> LENGTH: 4
<212> TYPE: PRT
<213> ORGANISM: Artificial Sequence
<220> FEATURE:
<223> OTHER INFORMATION: Variant of hinge region

<400> SEQUENCE: 9

Pro Ser Cys Pro
1

<210> SEQ ID NO 10
<211> LENGTH: 221
<212> TYPE: PRT
<213> ORGANISM: homo sapiens

<400> SEQUENCE: 10
```

```
Pro Ser Cys Pro Ala Pro Glu Phe Leu Gly Gly Pro Ser Val Phe Leu
1               5                   10                  15

Phe Pro Pro Lys Pro Lys Asp Thr Leu Met Ile Ser Arg Thr Pro Glu
            20                  25                  30

Val Thr Cys Val Val Val Asp Val Ser Gln Glu Asp Pro Glu Val Gln
        35                  40                  45

Phe Asn Trp Tyr Val Asp Gly Val Glu Val His Asn Ala Lys Thr Lys
    50                  55                  60

Pro Arg Glu Glu Gln Phe Asn Ser Thr Tyr Arg Val Val Ser Val Leu
65                  70                  75                  80

Thr Val Leu His Gln Asp Trp Leu Asn Gly Lys Glu Tyr Lys Cys Lys
                85                  90                  95

Val Ser Asn Lys Gly Leu Pro Ser Ser Ile Glu Lys Thr Ile Ser Lys
            100                 105                 110

Ala Lys Gly Gln Pro Arg Glu Pro Gln Val Tyr Thr Leu Pro Pro Ser
        115                 120                 125

Gln Glu Glu Met Thr Lys Asn Gln Val Ser Leu Thr Cys Leu Val Lys
    130                 135                 140

Gly Phe Tyr Pro Ser Asp Ile Ala Val Glu Trp Glu Ser Asn Gly Gln
145                 150                 155                 160

Pro Glu Asn Asn Tyr Lys Thr Thr Pro Pro Val Leu Asp Ser Asp Gly
                165                 170                 175

Ser Phe Phe Leu Tyr Ser Arg Leu Thr Val Asp Lys Ser Arg Trp Gln
            180                 185                 190

Glu Gly Asn Val Phe Ser Cys Ser Val Met His Glu Ala Leu His Asn
        195                 200                 205

His Tyr Thr Gln Lys Ser Leu Ser Leu Ser Leu Gly Lys
    210                 215                 220

<210> SEQ ID NO 11
<211> LENGTH: 11
<212> TYPE: PRT
<213> ORGANISM: Artificial Sequence
<220> FEATURE:
<223> OTHER INFORMATION: Variant of hinge region

<400> SEQUENCE: 11

Glu Ser Lys Tyr Gly Pro Pro Ser Cys Pro
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Variant of hinge region

<400> SEQUENCE: 12

Glu Ser Lys Tyr Gly Pro Pro Cys Pro Ser Pro
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Variant of hinge region

<400> SEQUENCE: 13
```

Glu Ser Lys Tyr Gly Pro Pro Cys Pro Ser
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Variant of hinge region

<400> SEQUENCE: 14

Glu Ser Lys Tyr Gly Pro Pro Cys Pro Pro
1               5                   10

<210> SEQ ID NO 15
<211> LENGTH: 8
<212> TYPE: PRT
<213> ORGANISM: Artificial Sequence
<220> FEATURE:
<223> OTHER INFORMATION: Variant of hinge region

<400> SEQUENCE: 15

Lys Tyr Gly Pro Pro Cys Pro Ser
1               5

<210> SEQ ID NO 16
<211> LENGTH: 8
<212> TYPE: PRT
<213> ORGANISM: Artificial Sequence
<220> FEATURE:
<223> OTHER INFORMATION: Variant of hinge region

<400> SEQUENCE: 16

Glu Ser Lys Tyr Gly Pro Pro Cys
1               5

<210> SEQ ID NO 17
<211> LENGTH: 7
<212> TYPE: PRT
<213> ORGANISM: Artificial Sequence
<220> FEATURE:
<223> OTHER INFORMATION: Variant of hinge region

<400> SEQUENCE: 17

Glu Lys Tyr Gly Pro Pro Cys
1               5

<210> SEQ ID NO 18
<211> LENGTH: 6
<212> TYPE: PRT
<213> ORGANISM: Artificial Sequence
<220> FEATURE:
<223> OTHER INFORMATION: Variant of hinge region

<400> SEQUENCE: 18

Glu Ser Pro Ser Cys Pro
1               5

<210> SEQ ID NO 19
<211> LENGTH: 5
<212> TYPE: PRT
<213> ORGANISM: Artificial Sequence
<220> FEATURE:
<223> OTHER INFORMATION: Variant of hinge region

<400> SEQUENCE: 19

Glu Pro Ser Cys Pro

-continued

```
1               5

<210> SEQ ID NO 20
<211> LENGTH: 4
<212> TYPE: PRT
<213> ORGANISM: Artificial Sequence
<220> FEATURE:
<223> OTHER INFORMATION: Variant of hinge region

<400> SEQUENCE: 20

Pro Ser Cys Pro
1

<210> SEQ ID NO 21
<211> LENGTH: 10
<212> TYPE: PRT
<213> ORGANISM: Artificial Sequence
<220> FEATURE:
<223> OTHER INFORMATION: Variant of hinge region

<400> SEQUENCE: 21

Glu Ser Lys Tyr Gly Pro Pro Ser Cys Pro
1               5                   10

<210> SEQ ID NO 22
<211> LENGTH: 9
<212> TYPE: PRT
<213> ORGANISM: Artificial Sequence
<220> FEATURE:
<223> OTHER INFORMATION: Variant of hinge region

<400> SEQUENCE: 22

Lys Tyr Gly Pro Pro Ser Cys Pro
1               5

<210> SEQ ID NO 23
<211> LENGTH: 9
<212> TYPE: PRT
<213> ORGANISM: Artificial Sequence
<220> FEATURE:
<223> OTHER INFORMATION: Variant of hinge region

<400> SEQUENCE: 23

Glu Ser Lys Tyr Gly Pro Ser Cys Pro
1               5

<210> SEQ ID NO 24
<211> LENGTH: 8
<212> TYPE: PRT
<213> ORGANISM: Artificial Sequence
<220> FEATURE:
<223> OTHER INFORMATION: Variant of hinge region

<400> SEQUENCE: 24

Glu Ser Lys Tyr Gly Pro Pro Cys
1               5
```

<210> SEQ ID NO 25
<211> LENGTH: 7
<212> TYPE: PRT
<213> ORGANISM: Artificial Sequence
<220> FEATURE:
<223> OTHER INFORMATION: Variant of hinge region

<400> SEQUENCE: 25

Lys Tyr Gly Pro Pro Cys Pro
1               5

<210> SEQ ID NO 26
<211> LENGTH: 7
<212> TYPE: PRT
<213> ORGANISM: Artificial Sequence
<220> FEATURE:
<223> OTHER INFORMATION: Variant of hinge region

<400> SEQUENCE: 26

Glu Ser Lys Pro Ser Cys Pro
1               5

<210> SEQ ID NO 27
<211> LENGTH: 6
<212> TYPE: PRT
<213> ORGANISM: Artificial Sequence
<220> FEATURE:
<223> OTHER INFORMATION: Variant of hinge region

<400> SEQUENCE: 27

Glu Ser Pro Ser Cys Pro
1               5

<210> SEQ ID NO 28
<211> LENGTH: 4
<212> TYPE: PRT
<213> ORGANISM: Artificial Sequence
<220> FEATURE:
<223> OTHER INFORMATION: Variant of hinge region

<400> SEQUENCE: 28

Glu Pro Ser Cys
1

METHOD FOR PREPARING LONG-ACTING DRUG CONJUGATE THROUGH PREPARATION OF INTERMEDIATE

CROSS REFERENCE TO RELATED APPLICATIONS

This Application is a National Stage of International Application No. PCT/KR2019/008912 filed Jul. 18, 2019.

SEQUENCE LISTING

The content of the electronically submitted sequence listing, file name: Sequence_Listing_As_Filed.txt; size: 9,132 bytes; and date of creation: Jan. 17, 2022, filed herewith, is incorporated herein by reference in its entirety.

TECHNICAL FIELD

The present invention relates to a novel intermediate for preparing a long-acting drug conjugate, a composition including the same, and a method for preparing the long-acting drug conjugate using the same.

BACKGROUND ART

Physiologically active polypeptides are easily denatured due to low stability, degraded by proteases in the blood, and easily removed by the kidneys or liver. Thus, in order to maintain blood concentration and titer of a protein drug containing a physiologically active polypeptide as a pharmacological component, the protein drug needs to be frequently administered to a patient. However, since most protein drugs are administered to patients in the form of an injection, frequent administration via injection to maintain blood concentration of the physiologically active polypeptide causes severe pain to the patients and increases costs for treatment. To solve these problems, efforts have been made to maximize the efficacy of protein drugs by increasing blood stability of the protein drugs and maintaining the blood concentration thereof at a high level for a long period of time. However, these long-acting formulations of protein drugs should not induce immune responses in patients while increasing the stability of the protein drugs and maintaining the titer of the drug at a sufficiently high level.

As a method of stabilizing proteins, inhibiting contact with proteases, and suppressing renal clearance, a method of chemically adding a highly soluble polymer such as polyethylene glycol (hereinafter referred to as "PEG") to the surfaces of protein drugs has conventionally been used. However, while the method of using PEG may extend in vivo duration of the peptide drug by increasing a molecular weight of PEG, the titer of the peptide drug significantly decreases as the molecular weight increases, and a yield may decrease due to low reactivity with the peptide.

Therefore, as a method for increasing serum half-life, a conjugate of an immunoglobulin fragment and a physiologically active polypeptide has been used, and various studies have been conducted to improve preparation methods therefor (Korean Patent Application Laid-open Publication No. 10-2014-0109342).

In particular, there has been a steadily increasing need for the development of efficient processes for preparing a long-acting drug conjugate by simplifying the existing preparation process.

DISCLOSURE

Technical Problem

An object of the present invention is to provide a novel intermediate for preparing a long-acting drug conjugate.

Another object of the present invention is to provide a composition for preparing a long-acting drug conjugate including the intermediate.

Another object of the present invention is to provide a method of preparing a long-acting drug conjugate using the intermediate.

Another object of the present invention is to provide a long-acting drug conjugate prepared by the preparation method.

Technical Solution

One aspect of the present invention provides a novel intermediate.

In an embodiment, the present invention provides a compound having a structure of Formula 1 below or a stereoisomer, a solvate, or a pharmaceutically acceptable salt thereof:

  [Formula 1]

wherein in Formula 1 above,

X is an immunoglobulin Fc region;

L1 is a straight or branched-chain $C_1$-$C_6$ alkylene;

L2 is -a1-CONH—, -a1-NHCO—, -a1-NHCO-a2-, —COO—, -b1-COO—, —COO-b2-, or -b1-COO-b2-, and a1, a2, b1, and b2 are each independently a straight or branched-chain $C_1$-$C_6$ alkylene;

n is from 10 to 2400; and

R is any one selected from the group consisting of 2,5-dioxopyrrolidinyl, 2,5-dioxopyrrolyl, aldehyde, maleimide, $C_6$-$C_{20}$ aryl disulfide, $C_5$-$C_{20}$ heteroaryl disulfide, vinyl sulfone, thiol, halogenated acetamide, succinimide, p-nitrophenyl carbonate, thioester, and derivatives thereof.

In the compound or a stereoisomer, a solvate, or a pharmaceutically acceptable salt thereof according to the previous embodiment, wherein in Formula 1, L1 is a straight or branched-chain $C_1$-$C_6$ alkylene; L2 is -a1-NHCO— or -a1-NHCO-a2-; a1 and a2 are each independently a straight or branched-chain $C_1$-$C_6$ alkylene; n is from 200 to 250; and R is maleimide.

In the compound or a stereoisomer, a solvate, or a pharmaceutically acceptable salt thereof according to any of the previous embodiments, the X is an immunoglobulin Fc region including a hinge sequence at the N-terminus.

In the compound or a stereoisomer, a solvate, or a pharmaceutically acceptable salt thereof according to any of the previous embodiments, the X includes a hinge sequence modified to include only one cysteine residue by deleting a part of an amino acid sequence of amino acids below:

Glu-Ser-Lys-Tyr-Gly-Pro-Pro-Cys-Pro-Ser-Cys-Pro (SEQ ID NO: 7).

In the compound or a stereoisomer, a solvate, or a pharmaceutically acceptable salt thereof according to any of the previous embodiments, the hinge sequence includes an amino acid sequence of SEQ ID NO: 8 (Ser-Cys-Pro) or an amino acid sequence of SEQ ID NO: 9 (Pro-Ser-Cys-Pro).

In the compound or a stereoisomer, a solvate, or a pharmaceutically acceptable salt thereof according to any of the previous embodiments, the L1 is linked to an amine or thiol reactive group located at one end of X.

In the compound or a stereoisomer, a solvate, or a pharmaceutically acceptable salt thereof according to any of the previous embodiments, the compound has a structure of Formula 2 below:

L1 is a straight or branched-chain $C_1$-$C_6$ alkylene;
L2 is -a1-NHCO— or -a1-NHCO-a2-;
a1 and a2 are each independently a straight or branched-chain $C_1$-$C_6$ alkylene;

[Formula 2]

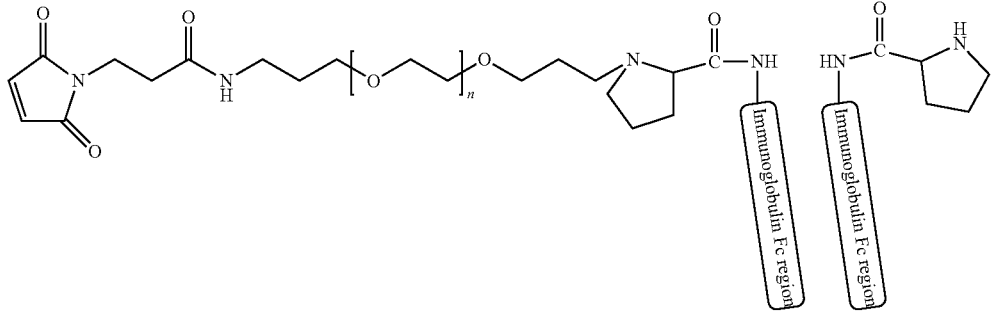

wherein in Formula 2, n is from 200 to 250.

In the compound or a stereoisomer, a solvate, or a pharmaceutically acceptable salt thereof according to any of the previous embodiments, the X is an immunoglobulin Fc region derived from IgG, IgA, IgD, IgE, or IgM.

In the compound or a stereoisomer, a solvate, or a pharmaceutically acceptable salt thereof according to any of the previous embodiments, the X is an immunoglobulin Fc region derived from IgG1, IgG2, IgG3, or IgG4.

In the compound or a stereoisomer, a solvate, or a pharmaceutically acceptable salt thereof according to any of the previous embodiments, the X is an immunoglobulin Fc region in a dimeric form.

In the compound or a stereoisomer, a solvate, or a pharmaceutically acceptable salt thereof according to any of the previous embodiments, the X is an immunoglobulin Fc region including an amino acid sequence of SEQ ID NO: 10.

In the compound or a stereoisomer, a solvate, or a pharmaceutically acceptable salt thereof according to any of the previous embodiments, the compound has a size of 40 kDa to 250 kDa.

Another aspect of the present invention provides a composition for preparing a long-acting drug conjugate including the compound, or a stereoisomer, a solvate, or a pharmaceutically acceptable salt thereof.

In an embodiment, the composition includes a compound of Formula 1 below or a stereoisomer, a solvate, or a pharmaceutically acceptable salt thereof, wherein the drug is a physiologically active polypeptide:

X-L1-(OCH$_2$CH$_2$)$_n$-O-L2-R    [Formula 1]

in Formula 1 above,
X is an immunoglobulin Fc region;
L1 is a straight or branched-chain $C_1$-$C_6$ alkylene;
L2 is -a1-CONH—, -a1-NHCO—, -a1-NHCO-a2-, —COO—, -b1-COO—, —COO-b2-, or -b1-COO-b2-, and a1, a2, b1, and b2 are each independently a straight or branched-chain $C_1$-$C_6$ alkylene;
n is from 10 to 2400; and
R is any one selected from the group consisting of 2,5-dioxopyrrolidinyl, 2,5-dioxopyrrolyl, aldehyde, maleimide, $C_6$-$C_{20}$ aryl disulfide, $C_5$-$C_{20}$ heteroaryl disulfide, vinyl sulfone, thiol, halogenated acetamide, succinimide, p-nitrophenyl carbonate, thioester, and derivatives thereof.

In the composition according to the previous embodiment, n is from 200 to 250; and
R is maleimide.

In the composition according to any of the previous embodiments, the physiologically active polypeptide is selected from the group consisting of glucagon-like peptide-1 (GLP-1), granulocyte colony stimulating factor (G-CSF), human growth hormone (hGH), erythropoietin (EPO), glucagon, insulin, growth hormone releasing hormone, growth hormone releasing peptide, interferons, interferon receptors, G-protein-coupled receptors, interleukins, interleukin receptors, enzymes, interleukin-binding protein, cytokine-binding protein, macrophage activating factor, macrophage peptide, B cell factor, T cell factor, protein A, allergy inhibitor, cell necrosis glycoprotein, immunotoxin, lymphotoxin, tumor necrosis factor, tumor suppressor, metastasis growth factor, α-1 antitrypsin, albumin, α-lactalbumin, apolipoprotein-E, highly glycosylated erythropoietin, angiopoietins, hemoglobin, thrombin, thrombin receptor activating peptide, thrombomodulin, blood factors VII, VIIa, VIII, IX, and XIII, plasminogen activating factor, fibrin-binding peptide, urokinase, streptokinase, hirudin, protein C, C-reactive protein, lenin inhibitor, collagenase inhibitor, superoxide dismutase, leptin, platelet-derived growth factor, epithelial growth factor, epidermal growth factor, angiostatin, angiotensin, bone growth factor, bone stimulating protein, calcitonin, atriopeptin, cartilage inducing factor, elcatonin, connective tissue activating factor, tissue factor pathway inhibitor, follicle stimulating hormone, luteinizing hormone, luteinizing hormone releasing hormone, nerve growth factor, parathyroid hormone, relaxin, secretin, somatomedin, insulin-like growth factor, adrenocortical hormone, cholecystokinin, pancreatic polypeptide, gastrin releasing peptide, corticotropin releasing factor, thyroid stimulating hormone, autotaxin, lactoferrin, myostatin, incretins, gastric inhibitory polypeptide (GIP), GLP-1/GIP dual agonist, GLP-1/GIP/Glucagon trigonal agonist, cell surface antigens, virus derived vaccine antigens, monoclonal antibodies, polyclonal antibodies, and antibody fragments.

In the composition according to any of the previous embodiments, R of the compound of the composition is linked to cysteine of the drug.

In the composition according to any of the previous embodiments, the X is an immunoglobulin Fc region derived from IgG1, IgG2, IgG3, or IgG4.

In the composition according to any of the previous embodiments, the X is an immunoglobulin Fc region including a hinge sequence modified to include only one cysteine residue by deleting a part of an amino acid sequence of amino acids below:

Glu-Ser-Lys-Tyr-Gly-Pro-Pro-Cys-Pro-Ser-Cys-Pro
(SEQ ID NO: 7).

Still another aspect of the present invention provides a method for preparing a long-acting conjugate of a physiologically active polypeptide.

In an embodiment, the preparation method includes preparing a conjugate by linking a mono-PEGylated immunoglobulin Fc region, prepared by linking a linker of Formula 3 below to the N-terminus of an immunoglobulin Fc region including a hinge sequence, to the physiologically active polypeptide:

CHO-L1-(OCH$_2$CH$_2$)$_n$O-L2-R     [Formula 3]

wherein in Formula 3,

L1 is a straight or branched-chain $C_1$-$C_6$ alkylene;

L2 is -a1-CONH—, -a1-NHCO—, -a1-NHCO-a2-, —COO—, -b1-COO—, —COO-b2-, or -b1-COO-b2-, and a1, a2, b1, and b2 are each independently a straight or branched-chain $C_1$-$C_6$ alkylene;

n is from 10 to 2400; and

R is any one selected from the group consisting of 2,5-dioxopyrrolidinyl, 2,5-dioxopyrrolyl, aldehyde, maleimide, $C_6$-$C_{20}$ aryl disulfide, $C_5$-$C_{20}$ heteroaryl disulfide, vinyl sulfone, thiol, halogenated acetamide, succinimide, p-nitrophenyl carbonate, thioester, and derivatives thereof.

In the preparation method according to the previous embodiment, the mono-PEGylated immunoglobulin Fc region is prepared by linking the linker of Formula 3 above to the N-terminus of the immunoglobulin Fc region at a pH of 4.0 to 8.0 in the presence of a reducing agent.

In the preparation method according to any of the previous embodiments, the conjugate is prepared by linking the linker of the mono-PEGylated immunoglobulin Fc region to the physiologically active polypeptide at a pH of 5.5 to 8.0.

In the preparation method according to any of the previous embodiments, the preparing of the conjugate is performed by reacting the mono-PEGylated immunoglobulin Fc region with the physiologically active polypeptide in a molar ratio of 1:1 to 1:3.

In the preparation according to any of the previous embodiments, the method includes: preparing a mono-PEGylated immunoglobulin Fc region by linking a linker of Formula 3 to the N-terminus of the immunoglobulin Fc region; and preparing a conjugate by linking the linker of the mono-PEGylated immunoglobulin Fc region prepared in the previous step to a physiologically active polypeptide.

In the preparation according to any of the previous embodiments, the linker of the mono-PEGylated immunoglobulin Fc region is linked to a cysteine of the physiologically active polypeptide.

In the preparation according to any of the previous embodiments, the method includes: preparing a mono-PEGylated immunoglobulin Fc region by linking a linker of Formula 3 to the N-terminus of an immunoglobulin Fc region; purifying the mono-PEGylated immunoglobulin Fc region prepared in the previous step by anion-exchange chromatography in a buffer solution with a pH of 6.0 to 8.5; and preparing a conjugate by linking the linker of the mono-PEGylated immunoglobulin Fc region purified in the previous step to a physiologically active polypeptide.

In the preparation according to any of the previous embodiments, the method is performed without ultrafiltration/diafiltration after preparing the mono-PEGylated immunoglobulin Fc region.

In the preparation according to any of the previous embodiments, the method further includes purifying the conjugate by hydrophobic interaction chromatography.

In the preparation according to any of the previous embodiments, in Formula 3, L1 is a straight or branched-chain $C_1$-$C_6$ alkylene; L2 is -a1-NHCO— or -a1-NHCO-a2-; a1 and a2 are each independently a straight or branched-chain $C_1$-$C_6$ alkylene; n is from 200 to 250; and R is maleimide.

In the preparation according to any of the previous embodiments, the linker has a structure of Formula 4 below:

[Formula 4]

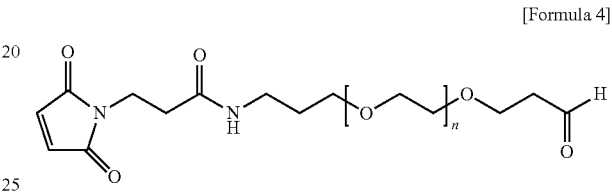

wherein in Formula 4, n is from 200 to 250.

In the preparation according to any of the previous embodiments, the linker has a size of 1 kDa to 100 kDa.

In the preparation according to any of the previous embodiments, the physiologically active polypeptide is selected from the group consisting of glucagon-like peptide-1 (GLP-1), granulocyte colony stimulating factor (G-CSF), human growth hormone (hGH), erythropoietin (EPO), glucagon, insulin, growth hormone releasing hormone, growth hormone releasing peptide, interferons, interferon receptors, G-protein-coupled receptors, interleukins, interleukin receptors, enzymes, interleukin-binding protein, cytokine-binding protein, macrophage activating factor, macrophage peptide, B cell factor, T cell factor, protein A, allergy inhibitor, cell necrosis glycoprotein, immunotoxin, lymphotoxin, tumor necrosis factor, tumor suppressor, metastasis growth factor, α-1 antitrypsin, albumin, α-lactalbumin, apolipoprotein-E, highly glycosylated erythropoietin, angiopoietins, hemoglobin, thrombin, thrombin receptor activating peptide, thrombomodulin, blood factors VII, VIIa, VIII, IX, and XIII, plasminogen activating factor, fibrin-binding peptide, urokinase, streptokinase, hirudin, protein C, C-reactive protein, lenin inhibitor, collagenase inhibitor, superoxide dismutase, leptin, platelet-derived growth factor, epithelial growth factor, epidermal growth factor, angiostatin, angiotensin, bone growth factor, bone stimulating protein, calcitonin, atriopeptin, cartilage inducing factor, elcatonin, connective tissue activating factor, tissue factor pathway inhibitor, follicle stimulating hormone, luteinizing hormone, luteinizing hormone releasing hormone, nerve growth factor, parathyroid hormone, relaxin, secretin, somatomedin, insulin-like growth factor, adrenocortical hormone, cholecystokinin, pancreatic polypeptide, gastrin releasing peptide, corticotropin releasing factor, thyroid stimulating hormone, autotaxin, lactoferrin, myostatin, incretins, gastric inhibitory polypeptide (GIP), GLP-1/GIP dual agonist, GLP-1/GIP/Glucagon trigonal agonist, cell surface antigens, virus derived vaccine antigens, monoclonal antibodies, polyclonal antibodies, and antibody fragments.

In the preparation according to any of the previous embodiments, the physiologically active polypeptide is a GLP-1/GIP/Glucagon trigonal agonist, glucagon, or an analog thereof.

In the preparation according to any of the previous embodiments, the physiologically active polypeptide includes one of amino acid sequences of SEQ ID NOS: 1 to 6.

In the preparation according to any of the previous embodiments, the hinge sequence is modified to include only one cysteine residue by deleting a part of a hinge sequence having an amino acid sequence below:
Glu-Ser-Lys-Tyr-Gly-Pro-Pro-Cys-Pro-Ser-Cys-Pro (SEQ ID NO: 7).

In the preparation according to any of the previous embodiments, the hinge sequence includes an amino acid sequence of SEQ ID NO: 8 (Ser-Cys-Pro) or an amino acid sequence of SEQ ID NO: 9 (Pro-Ser-Cys-Pro).

In the preparation according to any of the previous embodiments, the immunoglobulin Fc region is derived from IgG1, IgG2, IgG3, or IgG4.

Still another aspect of the present invention provides a long-acting drug conjugate prepared using the composition or the method.

Advantageous Effects

According to the method for preparing a long-acting drug conjugate using a novel intermediate according to the present invention, a long-acting drug conjugate may be prepared with a high yield although some of conventional purification processes are omitted, and thus productivity of the long-acting drug conjugate may be increased.

BRIEF DESCRIPTION OF DRAWINGS

FIG. 1 shows results of analyzing a structure of a mono-PEGylated immunoglobulin Fc region by MALDI-TOF assay.

BEST MODE

Hereinafter, embodiments of the present invention will be described in detail.

Meanwhile, each description and embodiment disclosed in the present invention may be applied herein to describe different descriptions and embodiments. In other words, all combinations of various components disclosed in the present invention are included within the scope of the present invention. Furthermore, the scope of the present invention should not be limited by the detailed description provided below.

Also, those skilled in the art will recognize or be able to ascertain, using no more than routine experimentation, many equivalents to specific embodiments of the present invention. Such equivalents are intended to be encompassed in the scope of the following claims.

Throughout the specification, not only the conventional one-letter and three-letter codes for naturally occurring amino acids, but also those three-letter codes generally allowed for other amino acids, such as α-aminoisobutyric acid (Aib), N-methylglycine (Sar), and α-methyl-glutamic acid are used. In addition, the amino acids mentioned herein are abbreviated according to the nomenclature rules of IUPAC-IUB as follows.
alanine Ala, A
arginine Arg, R
asparagine Asn, N
aspartic acid Asp, D
cysteine Cys, C
glutamic acid Glu, E
glutamine Gln, Q
glycine Gly, G
histidine His, H
isoleucine Ile, I
leucine Leu, L
lysine Lys, K
methionine Met, M
phenylalanine Phe, F
proline Pro, P
serine Ser, S
threonine Thr, T
tryptophan Trp, W
tyrosine Tyr, Y
valine Val, V An aspect of the present invention provides a compound having a structure of Formula 1 below, or a stereoisomer, a solvate, or a pharmaceutically acceptable salt thereof:

$$X\text{-L1-}(OCH_2CH_2)_n\text{O-L2-R} \qquad \text{[Formula 1]}$$

In Formula 1 above,

X is an immunoglobulin Fc region;

L1 is a straight or branched-chain $C_1$-$C_6$ alkylene;

L2 is -a1-CONH—, -a1-NHCO—, -a1-NHCO-a2-, —COO—, -b1-COO—, —COO-b2-, or -b1-COO-b2-, and a1, a2, b1, and b2 are each independently a straight or branched-chain $C_1$-$C_6$ alkylene;

n is from 10 to 2400; and

R is any one selected from the group consisting of 2,5-dioxopyrrolidinyl, 2,5-dioxopyrrolyl, aldehyde, maleimide, $C_6$-$C_{20}$ aryl disulfide, $C_5$-$C_{20}$ heteroaryl disulfide, vinyl sulfone, thiol, halogenated acetamide, succinimide, p-nitrophenyl carbonate, thioester, and derivatives thereof.

In the present invention, the compound having a structure of Formula 1, or a stereoisomer, a solvate, or a pharmaceutically acceptable salt thereof is a novel substance prepared for preparing a long-acting conjugate and may also be referred to as "intermediate" or "intermediate material" in the present application.

In a method of preparing a long-acting drug conjugate using the intermediate of the present invention, purification steps by ultrafiltration/diafiltration and hydrophobic interaction chromatography may be omitted, and effects on preparing the long-acting drug conjugate with a high yield may be obtained although the purification steps are omitted.

Specifically, the intermediate is in a form in which an immunoglobulin Fc region is linked to a linker. In the intermediate of Formula 1, X may be an immunoglobulin Fc region, and L1-$(OCH_2CH_2)_n$O-L2-R may be a linker. Specifically, in Formula 1 above, L1 is a straight or branched-chain $C_1$-$C_6$ alkylene; L2 is -a1-NHCO— or -a1-NHCO-a2-; a1 and a2 are each independently a straight or branched-chain $C_1$-$C_6$ alkylene; n is from 200 to 250; and R is maleimide, without being limited thereto.

The L1 is a site binding to the immunoglobulin Fc region and may be a straight or branched-chain $C_1$-$C_6$ alkylene, without being limited thereto. The L1 may be linked to an amine reactive group located at one end or a lysine residue of X or thiol reactive group, without being limited thereto. The R is a site for linkage between the intermediate and a physiologically active polypeptide and, specifically, may include a reactive group (e.g., thiol, maleimide, aldehyde, and succinimidyl) capable of binding to a cysteine, or an amine group of the N-terminus, or a lysine residue of a physiologically active polypeptide, without being limited thereto.

In the present invention, the intermediate may have a structure of Formula 2 below, but is not limited thereto:

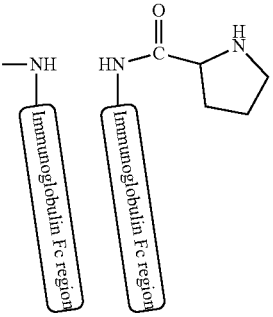

[Formula 2]

In Formula 2 above, n is from 1 to 3000, from 10 to 2000, from 50 to 1000, from 100 to 700, from 150 to 300, or from 200 to 250.

Specifically, the intermediate may have a size of 40 kDa to 250 kDa, 80 kDa to 200 kDa, or 100 kDa to 150 kDa, without being limited thereto.

In the present invention, the X may be an immunoglobulin Fc region having a hinge sequence at the N-terminus, and specifically, the hinge sequence may be modified to include only one cysteine residue by deleting a part of an amino acid sequence of the amino acid below, without being limited thereto:

Glu-Ser-Lys-Tyr-Gly-Pro-Pro-Cys-Pro-Ser-Cys-Pro (SEQ ID NO: 7).

As used herein, the term "immunoglobulin Fc region" refers to a region including a heavy chain constant domain 2 (CH2) and/or a heavy chain constant domain 3 (CH3) excluding the heavy chain and light chain variable domains of the immunoglobulin. The immunoglobulin Fc region may be a component constituting a moiety of the long-acting drug conjugate of the present invention.

Specifically, the X may be an immunoglobulin Fc region derived from IgG, IgA, IgD, IgE, or IgM, more specifically, an immunoglobulin Fc region derived from IgG1, IgG2, IgG3, or IgG4, without being limited thereto.

In the present invention, the immunoglobulin Fc region may include a particular hinge sequence at the N-terminus.

As used herein, the term "hinge sequence" refers to a site located at a heavy chain and forming a dimer of the immunoglobulin Fc region via an inter disulfide bond.

As used herein, the term "N-terminus" refers to amino terminus of a protein or polypeptide and may include an amino acid residue located at the end of the amino terminus or 1, 2, 3, 4, 5, 6, 7, 8, 9, 10 or more amino acids from the end of the amino terminus. The immunoglobulin Fc region of the present invention may include the hinge sequence at the N-terminus, without being limited thereto.

In view of the objects of the present invention, the hinge sequence may include only one cysteine residue as a cysteine residue located at the 8$^{th}$ or 11$^{th}$ position of the hinge sequence of SEQ ID NO: 7 is deleted. The hinge sequence of the present invention may consist of 3 to 12 amino acids including only one cysteine residue, without being limited thereto. More specifically, the hinge sequence of the present invention may have a sequence as follows: Glu-Ser-Lys-Tyr-Gly-Pro-Pro-Pro-Ser-Cys-Pro (SEQ ID NO: 11), Glu-Ser-Lys-Tyr-Gly-Pro-Pro-Cys-Pro-Ser-Pro (SEQ ID NO: 12), Glu-Ser-Lys-Tyr-Gly-Pro-Pro-Cys-Pro-Ser (SEQ ID NO: 13), Glu-Ser-Lys-Tyr-Gly-Pro-Pro-Cys-Pro-Pro (SEQ ID NO: 14), Lys-Tyr-Gly-Pro-Pro-Cys-Pro-Ser (SEQ ID NO: 15), Glu-Ser-Lys-Tyr-Gly-Pro-Pro-Cys (SEQ ID NO: 16), Glu-Lys-Tyr-Gly-Pro-Pro-Cys (SEQ ID NO: 17), Glu-Ser-Pro-Ser-Cys-Pro (SEQ ID NO: 18), Glu-Pro-Ser-Cys-Pro (SEQ ID NO: 19), Pro-Ser-Cys-Pro (SEQ ID NO: 20), Glu-Ser-Lys-Tyr-Gly-Pro-Pro-Ser-Cys-Pro (SEQ ID NO: 21), Lys-Tyr-Gly-Pro-Pro-Pro-Ser-Cys-Pro (SEQ ID NO: 22), Glu-Ser-Lys-Tyr-Gly-Pro-Ser-Cys-Pro (SEQ ID NO: 23), Glu-Ser-Lys-Tyr-Gly-Pro-Pro-Cys (SEQ ID NO: 24), Lys-Tyr-Gly-Pro-Pro-Cys-Pro (SEQ ID NO: 25), Glu-Ser-Lys-Pro-Ser-Cys-Pro (SEQ ID NO: 26), Glu-Ser-Pro-Ser-Cys-Pro (SEQ ID NO: 27), or Glu-Pro-Ser-Cys (SEQ ID NO: 28). More specifically, the hinge sequence may include an amino acid sequence of a sequence of SEQ ID NO: 8 (Ser-Cys-Pro) or a sequence of SEQ ID NO: 9 (Pro-Ser-Cys-Pro), without being limited thereto.

The X may be a dimer formed of two chain molecules of the immunoglobulin Fc region in the presence of the hinge sequence, and the intermediate of the present invention may be in a form in which one end of the linker is linked to one chain of the immunoglobulin Fc region in the dimeric form, without being limited thereto. In the present invention, the X may be a dimer of the immunoglobulin Fc region, but is not limited thereto.

In addition, X of the present invention may be an immunoglobulin Fc region including an amino acid sequence of SEQ ID NO: 10, without being limited thereto.

Meanwhile, the immunoglobulin Fc region of the present invention may be an extended Fc region including a part of or the entirety of a heavy chain constant domain 1 (CH1) and/or a light chain constant domain 1 (CL1) excluding the heavy chain and the light chain variable domains of the immunoglobulin, as long as the immunoglobulin Fc region has substantially identical or enhanced effects compared to the native type. Also, the immunoglobulin Fc region may be a region from which a considerably long part of the amino acid sequence corresponding to the CH2 and/or CH3 is removed.

For example, the immunoglobulin Fc region of the present invention may include 1) CH1 domain, CH2 domain, CH3 domain and CH4 domain, 2) CH1 domain and CH2 domain, 3) CH1 domain and CH3 domain, 4) CH2 domain and CH3 domain, 5) a combination of one or more domains selected from CH1 domain, CH2 domain, CH3 domain, and CH4 domain and an immunoglobulin hinge region (or a part of the hinge region), or 6) a dimer of each domain of the heavy chain constant domain and the light chain constant domain. However, the present invention is not limited thereto.

Also, the immunoglobulin Fc region of the present invention includes not only a naturally occurring amino acid sequence but also a sequence derivative thereof. The amino acid sequence derivative refers to a sequence different from the naturally occurring amino acid sequence due to a deletion, insertion, non-conservative or conservative substitution, or any combination of one or more amino acids of the naturally occurring amino acid sequence.

For example, in the case of IgG Fc, amino acid residues known to be important in linkage at positions 214 to 238, 297 to 299, 318 to 322, or 327 to 331 may be used as a suitable target for modification.

Also, other various derivatives including those in which a site capable of forming a disulfide bond is deleted or certain amino acid residues are eliminated from the N-terminus of a native Fc form, and a methionine residue is added to the N-terminus of the native Fc form may be used. In addition, to remove effector functions, a complement binding site, such as a C1q binding site, may be deleted, and an antibody dependent cell mediated cytotoxicity (ADCC) site may be deleted. Techniques of preparing such sequence derivatives of the immunoglobulin Fc region are disclosed in International Patent Publication Nos. WO 97/34631 and WO 96/32478.

Amino acid exchanges in proteins and peptides, which do not generally alter the activity of molecules, are known in the art (H. Neurath, R. L. Hill, *The Proteins*, Academic Press, New York, 1979). The most commonly occurring exchanges of amino acid residues are exchanges between Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly. If required, the Fc region may be modified by phosphorylation, sulfation, acrylation, glycosylation, methylation, farnesylation, acetylation, and amidation.

The above-described sequence derivatives of the Fc region are derivatives that have a biological activity equivalent to that of the immunoglobulin Fc region of the present invention or improved structural stability against heat, pH, or the like.

In addition, these immunoglobulin Fc regions may be obtained from native forms isolated from humans and other animals including cows, goats, swine, mice, rabbits, hamsters, rats and guinea pigs, or may be recombinants or derivatives thereof, obtained from transformed animal cells or microorganisms. In this regard, they may be obtained from a native immunoglobulin by isolating whole immunoglobulins from living humans or animals and treating them with a protease. Papain digests the native immunoglobulin into Fab and Fc regions and pepsin digests the native immunoglobulin into pF'c and F(ab)$_2$ fragments. These fragments may be subjected to size-exclusion chromatography to isolate Fc or pF'c. In a more specific embodiment, a human-derived Fc region is a recombinant immunoglobulin Fc region obtained from a microorganism.

In addition, the immunoglobulin Fc region of the present invention may have natural glycans or increased or decreased glycans compared to the natural type, or be in a deglycosylated form. The increase, decrease, or removal of glycans of the immunoglobulin Fc may be achieved by any methods commonly used in the art such as a chemical method, an enzymatic method, and a genetic engineering method using a microorganism. In this regard, the immunoglobulin Fc region obtained by removing glycans shows a significant decrease in binding affinity to a complement c1q and a decrease in or loss of antibody-dependent cytotoxicity or complement-dependent cytotoxicity, and thus unnecessary immune responses are not induced thereby in living organisms. Based thereon, a deglycosylated or aglycosylated immunoglobulin Fc region may be more suitable as a drug carrier in view of the objects of the present invention.

As used herein, the term "deglycosylation" refers to a Fc region from which glycan is removed using an enzyme and the term "aglycosylation" refers to a Fc region that is not glycosylated and produced in prokaryotes, more specifically, *E. coli*.

Meanwhile, the immunoglobulin Fc region may be derived from humans or animals such as cows, goats, swine, mice, rabbits, hamsters, rats, or guinea pigs. In a more specific embodiment, the immunoglobulin Fc region may be derived from humans.

In addition, the immunoglobulin Fc region may be derived from IgG, IgA, IgD, IgE, or IgM, or any combination or hybrid thereof. In a more specific embodiment, the immunoglobulin Fc region is derived from IgG or IgM which are the most abundant proteins in human blood, and in an even more specific embodiment, it is derived from IgG known to enhance the half-lives of ligand-binding proteins. In a yet even more specific embodiment, the immunoglobulin Fc region is an IgG4 Fc region, and in the most specific embodiment, the immunoglobulin Fc region is an aglycosylated Fc region derived from human IgG4, without being limited thereto.

Meanwhile, as used herein, the term "combination" related to the immunoglobulin Fc region refers to formation of a linkage between a polypeptide encoding a single-chain immunoglobulin Fc region of the same origin and a single-chain polypeptide of a different origin when a dimer or a multimer is formed. That is, a dimer or multimer may be prepared using two or more Fc fragments selected from the group consisting of IgG Fc, IgA Fc, IgM Fc, IgD Fc, and IgE Fc fragments.

As used herein, the term "hybrid" means that sequences corresponding to two or more immunoglobulin Fc regions of different origins are present in a single-chain of an immunoglobulin constant domain. In the present invention, various hybrid forms are possible. That is, a domain hybrid may be composed of 1 to 4 domains selected from the group consisting of CH1, CH2, CH3, and CH4 of IgG Fc, IgM Fc, IgA Fc, IgE Fc, and IgD Fc and may further include a hinge region.

Meanwhile, IgG may also be classified into IgG1, IgG2, IgG3 and IgG4 subclasses, which may be combined or hybridized in the present invention. Preferred are IgG2 and IgG4 subclasses, and most preferred is the Fc fragment of IgG4 rarely having effector functions such as complement dependent cytotoxicity (CDC).

As used herein, the term "linker" refers to a moiety linking a drug (e.g., physiologically active polypeptide) to the immunoglobulin Fc region in the long-acting drug conjugate, and the linker may be a peptidyl linker or a non-peptidyl linker. Specifically, the linker may be represented by Formula 3 below, without being limited thereto:

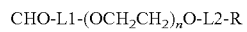  [Formula 3]

In Formula 3,

L1 is a straight or branched-chain $C_1$-$C_6$ alkylene;

L2 is -a1-CONH—, -a1-NHCO—, -a1-NHCO-a2-, —COO—, -b1-COO—, —COO-b2-, or -b1-COO-b2-, and a1, a2, b1, and b2 are each independently a straight or branched-chain $C_1$-$C_6$ alkylene;

n is from 1 to 3000, from 10 to 2000, from 50 to 1000, from 100 to 700, from 150 to 300, or from 200 to 250; and R is any one selected from the group consisting of 2,5-dioxopyrrolidinyl, 2,5-dioxopyrrolyl, aldehyde, maleimide, $C_6$-$C_{20}$ aryl disulfide, $C_5$-$C_{20}$ heteroaryl disulfide, vinyl sulfone, thiol, halogenated acetamide, succinimide, p-nitrophenyl carbonate, thioester, and derivatives thereof.

The linker may include polyethylene glycol and has particular chemical structures at both ends of polyethylene glycol, without being limited thereto.

Specifically, in Formula 3 above, L1 may be a straight or branched-chain $C_1$-$C_6$ alkylene; L2 may be -a1-NHCO— or -a1-NHCO-a2-; a1 and a2 may be each independently a straight or branched-chain $C_1$-$C_6$ alkylene; n may be from 200 to 250; and R may be maleimide, and the linker may have a size of 1 kDa to 200 kDa, 1 kDa to 150 kDa, 1 kDa to 100 kDa, 1 kDa to 50 kDa, or 1 kDa to 10 kDa, but is not limited thereto.

Also, the linker may have a structure of Formula 4 below, without being limited thereto:

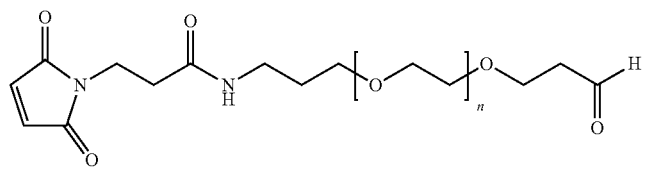

[Formula 4]

In Formula 4 above, n may be from 1 to 3000, from 10 to 2000, from 50 to 1000, from 100 to 700, from 150 to 300, or from 200 to 250.

One end of the linker may be linked to the immunoglobulin Fc region, specifically, the N-terminus of the immunoglobulin Fc region, more specifically, the hinge sequence located at the N-terminus of the immunoglobulin Fc region, even more specifically, a proline residue of the hinge sequence, to form the intermediate, but is not limited thereto.

In the present invention, the term "pharmaceutically acceptable" refers to a substance that may be effectively used for the intended use within the scope of pharmacomedical decision without inducing excessive toxicity, irritation, or allergic responses.

As used herein, the term "pharmaceutically acceptable salt" refers to a salt derived from a pharmaceutically acceptable inorganic acid, organic acid, or base. Examples of a suitable acid may include hydrochloric acid, bromic acid, sulfuric acid, nitric acid, perchloric acid, fumaric acid, maleic acid, phosphoric acid, glycolic acid, lactic acid, salicylic acid, succinic acid, toluene-p-sulfonic acid, tartaric acid, acetic acid, citric acid, methanesulfonic acid, formic acid, benzoic acid, malonic acid, naphthalene-2-sulfonic acid, and benzenesulfonic acid. Examples of the salt derived from a suitable base may include alkali metals such as sodium and potassium, alkali earth metals such as magnesium, and ammonium.

The present invention includes not only the compound or a pharmaceutically acceptable salt thereof, but also a solvate prepared therefrom.

In addition, the compound may be present in the form of an enantiomer (R or S isomer), racemate, or diastereomer, or any mixture thereof in the case of having an asymmetric carbon center (absent carbon) in a substituent thereof. In addition, the compound may be present in the form of an exo or endo isomer in the case of having a bridged ring, without being limited thereto.

An aspect of the present invention provides a composition including a compound having a structure of Formula 1 below, or a stereoisomer, a solvate, or a pharmaceutically acceptable salt thereof, wherein the drug is a physiologically active polypeptide:

X-L1-(OCH$_2$CH$_2$)$_n$O-L2-R    [Formula 1]

In Formula 1 above,

X is an immunoglobulin Fc region;

L1 is a straight or branched-chain $C_1$-$C_6$ alkylene;

L2 is -a1-CONH—, -a1-NHCO—, -a1-NHCO-a2-, —COO—, -b1-COO—, —COO-b2-, or -b1-COO-b2-, and a1, a2, b1, and b2 are each independently a straight or branched-chain $C_1$-$C_6$ alkylene;

n is from 1 to 3000, from 10 to 2000, from 50 to 1000, from 100 to 700, from 150 to 300, or from 200 to 250; and R is any one selected from the group consisting of 2,5-dioxopyrrolidinyl, 2,5-dioxopyrrolyl, aldehyde, maleimide, $C_6$-$C_{20}$ aryl disulfide, $C_5$-$C_{20}$ heteroaryl disulfide, vinyl sulfone, thiol, halogenated acetamide, succinimide, p-nitrophenyl carbonate, thioester, and derivatives thereof.

Specifically, in Formula 1 above, L1 is a straight or branched-chain $C_1$-$C_6$ alkylene; L2 is -a1-NHCO— or -a1-NHCO-a2-; a1 and a2 are each independently a straight or branched-chain $C_1$-$C_6$ alkylene; n is from 200 to 250; and R is maleimide, without being limited thereto.

The composition of the present invention includes the intermediate and has a use for preparing a long-acting drug conjugate.

Specifically, since the composition of the present invention includes the intermediate in which the linker is linked to the immunoglobulin Fc region, the composition of the present invention may be reacted with a physiologically active polypeptide such that the linker of the intermediate is linked to the physiologically active polypeptide, thereby preparing a long-acting drug conjugate. More specifically, the long-acting drug conjugate may be prepared via linkage between R of Formula 1 corresponding to one end of the linker and a cysteine, or an amine group such as the N-terminus, or a lysine residue of the physiologically active polypeptide, without being limited thereto.

In the present invention, any physiologically active polypeptide of the long-acting drug conjugate that may be prepared using the composition may fall within the scope of the present invention regardless of type, size, origin, and the like as long as the physiologically active polypeptide has pharmacological effects on disease. Examples of the physiologically active polypeptide may include glucagon-like peptide-1 (GLP-1), granulocyte colony stimulating factor (G-CSF), human growth hormone (hGH), erythropoietin (EPO), glucagon, insulin, growth hormone releasing hormone, growth hormone releasing peptide, interferons, interferon receptors, G-protein-coupled receptors, interleukins, interleukin receptors, enzymes, interleukin-binding protein, cytokine-binding protein, macrophage activating factor, macrophage peptide, B cell factor, T cell factor, protein A, allergy inhibitor, cell necrosis glycoprotein, immunotoxin, lymphotoxin, tumor necrosis factor, tumor suppressor, metastasis growth factor, α-1 antitrypsin, albumin, α-lactalbumin, apolipoprotein-E, highly glycosylated erythropoietin, angiopoietins, hemoglobin, thrombin, thrombin receptor activating peptide, thrombomodulin, blood factors VII, VIIa, VIII, IX, and XIII, plasminogen activating factor, fibrin-binding peptide, urokinase, streptokinase, hirudin, protein C, C-reactive protein, lenin inhibitor, collagenase inhibitor, superoxide dismutase, leptin, platelet-derived growth factor, epithelial growth factor, epidermal growth factor, angiostatin, angiotensin, bone growth factor, bone stimulating protein, calcitonin, atriopeptin, cartilage inducing factor, elcatonin, connective tissue activating factor, tissue factor pathway inhibitor, follicle stimulating hormone, luteinizing hormone, luteinizing hormone releasing hormone, nerve growth factor, parathyroid hormone, relaxin, secretin, somatomedin, insulin-like growth factor, adrenocortical hormone, cholecystokinin, pancreatic polypeptide, gastrin releasing peptide, corticotropin releasing factor, thyroid stimulating hormone, autotaxin, lactoferrin, myostatin, incretins, gastric inhibitory polypeptide (GIP), GLP-1/GIP dual agonist, GLP-1/GIP/Glucagon trigonal agonist, cell surface antigens, virus derived vaccine antigens, monoclonal antibodies, polyclonal antibodies, and antibody fragments, but are not limited thereto.

More specifically, the physiologically active polypeptide may be glucagon-like peptide-1 (GLP-1), glucagon, insulin, enzyme, incretin, gastric inhibitory polypeptide (GIP), GLP-1/GIP dual agonist, or GLP-1/GIP/Glucagon triple agonist, but is not limited thereto.

Because a method for preparing a long-acting drug conjugate using the intermediate or the composition including the same according to the present invention is performed by linking the intermediate, in which the linker is linked to the immunoglobulin Fc region, to the physiologically active polypeptide, any physiologically active polypeptide including an amino acid residue or a reactive group capable of binding to the intermediate may be used regardless of types thereof to prepare the long-acting drug conjugate using the intermediate or the composition including the same of the present invention.

In the present invention, the X may be an immunoglobulin Fc region derived from IgG1, IgG2, IgG3, or IgG4, without being limited thereto.

In addition, the X may be an immunoglobulin Fc region including a hinge sequence modified to include only one cysteine residue by deleting a part of an amino acid sequence of amino acids below, but is not limited thereto:

Glu-Ser-Lys-Tyr-Gly-Pro-Pro-Cys-Pro-Ser-Cys-Pro (SEQ ID NO: 7).

In the case of using the composition of the present invention, the long-acting drug conjugate may be prepared without performing ultrafiltration/diafiltration and one cycle of hydrophobic interaction chromatography may be optionally omitted.

Specifically, when the long-acting drug conjugate is prepared by reacting the intermediate or the composition including the same according to the present invention with the drug, purity of the long-acting drug conjugate may be 70%, 80%, 85%, 90%, 91%, 92%, 93%, 94%, 95%, 96%, 97%, 98%, or 99% or more, but is not limited thereto. The purity may be measured by any method well known in the art, specifically, by SE-HPLC, RP-HPLC, and IE-HPLC, but any method available in the art. More specifically, the purity of the long-acting drug conjugate prepared using the composition of the present invention may be 90% or more in SE-HPLC, 80% or more in RP-HPLC, and 85% or more in IE-HPLC, but is not limited thereto.

Also, the composition of the present invention may further include a buffer, a stabilizer, a preservative, a salt, and the like required to stabilize the intermediate and to prepare the long-acting drug conjugate, but is not limited thereto.

Another aspect of the present invention provides a kit for preparing a long-acting drug conjugate including the composition. The kit may include a reagent, manual and the like for preparing the long-acting drug conjugate, without being limited thereto.

Another aspect of the present invention provides a method for preparing a long-acting drug conjugate.

The preparation method of the present invention is a method for preparing a long-acting drug conjugate in which a drug is linked to an immunoglobulin Fc region via a linker, specifically, a method for preparing a long-acting drug conjugate by linking the intermediate to the drug, without being limited thereto.

Specifically, the preparation method is characterized by sequentially performing i) linking a linker including polyethylene glycol (PEG) to an immunoglobulin Fc region, and ii) linking the linker, which is linked to the immunoglobulin Fc region, to a drug (e.g., a physiologically active polypeptide or protein). That is, the preparation method is characterized by performing steps in a particular order, i.e., performing a first step of preparing the intermediate by linking the linker including PEG to the immunoglobulin Fc region, and then performing a second step of linking the drug to the intermediate. Alternatively, the preparation method of the present invention may also be performed only by the second step of preparing the long-acting drug conjugate via a reaction between the intermediate or the composition for preparing the long-acting drug conjugate including the same and the drug, without performing the first step, but is not limited thereto. This preparation method may be referred to as "reverse order preparation method" in the present application.

In the present invention, in the case of the method for preparing the long-acting drug conjugate performed by preparing the intermediate first and then linking the intermediate to the drug, the purification processes by ultrafiltration/diafiltration and hydrophobic interaction chromatography may be omitted and it was confirmed that the long-acting drug conjugate may be prepared with a high yield although the purification processes are omitted.

According to the convention preparation method in which the linker is first linked to the physiologically active polypeptide and then linked to the immunoglobulin Fc region without forming the intermediate, when the physiologically active polypeptide-linked linker (e.g., polyethylene glycol) is linked to the immunoglobulin Fc region, ultrafiltration/diafiltration is required as a separate process after the linker is linked to the physiologically active polypeptide and before the linked product is linked to the immunoglobulin Fc region to reduce the risk of aggregation that may occur due to low pH conditions (pH of about 3.0) of an equilibrium buffer and an elution buffer used for purification of the physiologically active polypeptide-linked linker and to adjust the pH conditions for reaction using an appropriate buffer. On the contrary, in the preparation method according to the present invention in which the intermediate is prepared by linking the linker to the immunoglobulin Fc region first, a pH of a buffer used in purification of the immunoglobulin Fc region-linked linker is relatively high, and thus the ultrafiltration/diafiltration process may be omitted and then a process of linking the immunoglobulin Fc region-linked linker to the physiologically active polypeptide may be performed.

Therefore, in the preparation method of the present invention, ultrafiltration/diafiltration may not be performed after preparing a mono-PEGylated immunoglobulin Fc region, but the present invention is not limited thereto. In the method for preparing a long-acting drug conjugate according to the present invention, a pH of a solution used to purify the mono-PEGylated immunoglobulin Fc region is not significantly different from a pH of a solution used for a subsequent reaction so that linkage to the drug may be performed without conducting the ultrafiltration/diafiltration. By omitting the ultrafiltration/diafiltration process, the risk of formation of aggregate impurities in a concentration step may be reduced and the preparation process may be simplified so that cost reduction effects may be expected in the case where the technology is commercialized.

Also, the preparation method of the present invention may further include purifying the conjugate by hydrophobic interaction chromatography, without being limited thereto.

Specifically, the hydrophobic interaction chromatography may be performed only once or more than once in accordance with properties of the drug of the long-acting drug conjugate and type and size of the linker.

According to the preparation method of the present invention, not only an amount of the expensive drug may be reduced but also an amount of unreacted immunoglobulin Fc regions may be reduced, so that the entire or a part of the purification process by hydrophobic interaction chromatography may be omitted to obtain effects on reducing raw materials required for preparation of the long-acting drug conjugate and costs therefor compared to the conventional method.

Meanwhile, although the ultrafiltration/diafiltration and hydrophobic interaction chromatography processes, which have been performed in the conventional method for preparing the long-acting drug conjugate, are omitted and only the final purification process (e.g., one cycle of hydrophobic interaction chromatography) is performed in the preparation method of the present invention, it is advantageous in that a purity of the final conjugate obtained by the present invention is maintained compared to that of the conventional preparation method. That is, according to the preparation method of the present invention, the final purity may be maintained although some of the purification processes are omitted so that productivity of the long-acting drug conjugate may be improved.

The purity of the long-acting drug conjugate according to the present invention may be measured by any method well known in the art and examples of the method may be SE-HPLC, RP-HPLC, and IE-HPLC, without being limited thereto.

According to the preparation method of the present invention, the final purity of the long-acting drug conjugate may be 90% or more, specifically, 91%, 92%, 93%, 94%, 95%, 96%, 97%, 98%, or 99% or more, without being limited thereto.

Meanwhile, in the preparation method of the present invention, the mono-PEGylated immunoglobulin Fc region is prepared first and then linked to the physiologically active polypeptide, so that the long-acting drug conjugate may be prepared with a higher yield compared to the conventional method in terms of not only the physiologically active polypeptide but also the immunoglobulin Fc region.

In an embodiment of the present invention, it was confirmed that the yield of the long-acting drug conjugate obtained by the preparation method of the present invention was increased twice or more compared to the yield of the long-acting drug conjugate obtained by the conventional method.

Specifically, the preparation method of the present invention relates to a method for preparing a long-acting drug conjugate including preparing a conjugate by linking a mono-PEGylated immunoglobulin Fc region, which is prepared by linking a linker of Formula 3 below to the N-terminus of an immunoglobulin Fc region including a hinge sequence, to a drug (physiologically active polypeptide:

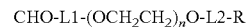  [Formula 3]

In Formula 3 above,

L1 is a straight or branched-chain $C_1$-$C_6$ alkylene;

L2 is -a1-CONH—, -a1-NHCO—, -a1-NHCO-a2-, —COO—, -b1-COO—, —COO-b2-, or -b1-COO-b2-, and a1, a2, b1, and b2 are each independently a straight or branched-chain $C_1$-$C_6$ alkylene;

n is from 10 to 2400; and

R is any one selected from the group consisting of 2,5-dioxopyrrolidinyl, 2,5-dioxopyrrolyl, aldehyde, maleimide, $C_6$-$C_{20}$ aryl disulfide, $C_5$-$C_{20}$ heteroaryl disulfide, vinyl sulfone, thiol, halogenated acetamide, succinimide, p-nitrophenyl carbonate, thioester, and derivatives thereof, without being limited thereto.

More specifically, the preparation method may include: preparing a mono-PEGylated immunoglobulin Fc region by linking a linker of Formula 3 above to the N-terminus of an immunoglobulin Fc region; and preparing a conjugate by linking the linker of the mono-PEGylated immunoglobulin Fc region prepared in the above-described step to a physiologically active polypeptide, or the preparation method may include: preparing a mono-PEGylated immunoglobulin Fc region by linking a linker of Formula 3 to the N-terminus of an immunoglobulin Fc region; purifying the mono-PEGylated immunoglobulin Fc region prepared in the above-described step by anion-exchange chromatography in a buffer solution with a pH of 6.0 to 8.5, a pH of 6.0 to 8.0, a pH of 6.0 to 7.5, a pH of 6.0 to 7.0, a pH of 6.1 to 6.9, a pH of 6.2 to 6.8, or a pH of 6.3 to 6.7; and preparing a conjugate by linking the linker of the mono-PEGylated immunoglobulin Fc region purified in the above-described step to a physiologically active polypeptide, without being limited thereto.

In addition, in the preparation method of the present invention, (i) the mono-PEGylated immunoglobulin Fc region may be prepared by linking the linker of Formula 3 to the N-terminus of the immunoglobulin Fc region in the presence of a reducing agent at a pH of 4.0 to 8.0, a pH of 4.5 to 7.5, a pH of 5.5 to 7.5, a pH of 5.6 to 7.4, a pH of 5.7 to 7.3 or a pH of 5.8 to 7.2; and/or (ii) the conjugate may be prepared by linking the linker of the mono-PEGylated immunoglobulin Fc region to the physiologically active polypeptide at a pH of 5.5 to 8.0, a pH of 6.0 to 7.5, or a pH of 6.5 to 7.5, without being limited thereto.

In addition, the step of preparing the conjugate according to the preparation method of the present invention may be performed by reacting the physiologically active polypeptide in an amount equivalent to or more than an amount of the mono-PEGylated immunoglobulin Fc region, and specifically, a molar ratio of mono-PEGylated immunoglobulin Fc region:physiologically active polypeptide may be from 1:1 to 1:10, from 1:1 to 1:7, from 1:1 to 1:5, or from 1:1 to 1:3, but is not limited thereto.

As used herein, the term "mono-PEGylated immunoglobulin Fc region" refers to an intermediate material that is produced in the middle of the method for preparing the long-acting drug conjugate according to the present invention in which one linker including one polyethylene glycol is linked to the immunoglobulin Fc region. That is, in the present invention, the "mono-PEGylated immunoglobulin Fc region" may be used interchangeably with "intermediate" or "intermediate material".

In the present invention, the immunoglobulin Fc region may be an immunoglobulin Fc region derived from IgG1, IgG2, IgG3, or IgG4, without being limited thereto.

In addition, the immunoglobulin Fc region may be an immunoglobulin Fc region including a hinge sequence modified to include only one cysteine residue by deleting a part of an amino acid sequence below, and specifically, the hinge sequence may include an amino acid sequence of SEQ ID NO: 8 (Ser-Cys-Pro) or SEQ ID NO: 9 (Pro-Ser-Cys-Pro), without being limited thereto.

Glu-Ser-Lys-Tyr-Gly-Pro-Pro-Cys-Pro-Ser-Cys-Pro (SEQ ID NO: 7).

The "long-acting drug conjugate" of the present invention refers to a drug conjugate having a structure in which a drug (physiologically active polypeptide) having a pharmacological activity in the body is linked to an immunoglobulin Fc region via a linker and an increased half-life. In view of the objects of the present invention, the long-acting drug conjugate may be one in which the intermediate or mono-PEGylated immunoglobulin Fc region is linked to the drug, but is not limited thereto.

Specifically, the drug is not limited to particular substances as long as the drug has preventive, therapeutic, or alleviating effects on a certain disease and may be a natural or non-natural protein, enzyme, antibody, compound, or the likes. More specifically, the drug may be a physiologically active polypeptide or protein, even more specifically, the physiologically active polypeptide may be glucagon-like peptide-1 (GLP-1), granulocyte colony stimulating factor (G-CSF), human growth hormone (hGH), erythropoietin (EPO), glucagon, insulin, growth hormone releasing hormone, growth hormone releasing peptide, interferons, interferon receptors, G-protein-coupled receptors, interleukins, interleukin receptors, enzymes, interleukin-binding protein, cytokine-binding protein, macrophage activating factor, macrophage peptide, B cell factor, T cell factor, protein A, allergy inhibitor, cell necrosis glycoprotein, immunotoxin, lymphotoxin, tumor necrosis factor, tumor suppressor, metastasis growth factor, α-1 antitrypsin, albumin, α-lactalbumin, apolipoprotein-E, highly glycosylated erythropoietin, angiopoietins, hemoglobin, thrombin, thrombin receptor activating peptide, thrombomodulin, blood factors VII, VIIa, VIII, IX, and XIII, plasminogen activating factor, fibrin-binding peptide, urokinase, streptokinase, hirudin, protein C, C-reactive protein, lenin inhibitor, collagenase inhibitor, superoxide dismutase, leptin, platelet-derived growth factor, epithelial growth factor, epidermal growth factor, angiostatin, angiotensin, bone growth factor, bone stimulating protein, calcitonin, atriopeptin, cartilage inducing factor, elcatonin, connective tissue activating factor, tissue factor pathway inhibitor, follicle stimulating hormone, luteinizing hormone, luteinizing hormone releasing hormone, nerve growth factor, parathyroid hormone, relaxin, secretin, somatomedin, insulin-like growth factor, adrenocortical hormone, cholecystokinin, pancreatic polypeptide, gastrin releasing peptide, corticotropin releasing factor, thyroid stimulating hormone, autotaxin, lactoferrin, myostatin, incretins, gastric inhibitory polypeptide (GIP), GLP-1/GIP dual agonist, GLP-1/GIP/Glucagon trigonal agonist, cell surface antigens, virus derived vaccine antigens, monoclonal antibodies, polyclonal antibodies, and antibody fragments, but are not limited thereto. More specifically, the physiologically active polypeptide may be GLP-1/GIP/Glucagon trigonal agonist, glucagon, or a analog thereof, but is not limited thereto. Even more specifically, the physiologically active polypeptide may include, essentially consist of, or consist of one of amino acid sequences of SEQ ID NOS: 1 to 6, but is not limited thereto.

In addition, any variants, derivatives, and fragments of the physiologically active polypeptide also fall within the scope of the present invention.

As used herein, the term "variant" refers to a peptide having an amino acid sequence in which one or more amino acids are different from those of a native physiologically active polypeptide while retaining the same functions as those of the native physiologically active polypeptide, and the variant may be prepared by substitution, addition, deletion, modification, or any combination of some amino acids of the amino acid sequence of the native physiologically active polypeptide.

As used herein, the term "derivative" refers to a peptide, a peptide analog, or a peptidomimetic obtained by modifying one or more amino acids of the native physiologically active polypeptide by addition, deletion, or substitution to have similar activity to that of the native physiologically active polypeptide.

As used herein, the term "fragment" refers to a form obtained by adding/deleting one or more amino acids to/from the N-terminus or the C-terminus, and the added amino acid may be any amino acid that does not exist in nature (e.g.; D-amino acid).

The methods for preparing the variant, derivative, and fragment of the physiologically active polypeptide may be used independently or in combination. For example, any physiologically active polypeptide having one or more different amino acids in the amino acid sequence and deamination of an amino acid residue at the N-terminus may be included therein.

The derivative of the physiologically active polypeptide includes biosimilar and biobetter forms. For example, with respect to biosimilars, the biosimilar may be any biosimilar enzyme available in the long-acting drug conjugate of the present invention although there is a difference between a known enzyme and a host for its expression, a difference in glycosylation feature and the degree thereof, and a difference in the degree of substitution in a particular amino acid residue of the corresponding enzyme in light of the standard sequence where the degree of substitution is not 100% substitution. The physiologically active polypeptide and the variant, derivative and fragment thereof may be produced from animal cells, E. coli, yeast, insect cells, plant cells, living animals, and the like via genetic recombination, the production methods are not limited thereto, and any commercially available physiologically active polypeptides, and variants, derivatives, and fragments thereof may also be used.

In addition, the physiologically active polypeptide, and the variant, derivative and fragment thereof may include an amino acid sequence having a homology of at least 80%, specifically, at least 90%, more specifically, at least 91%, 92%, 93%, 94%, 95%, 96%, 97%, 98%, or 99%, and the physiologically active polypeptide, and the variant, derivative, and fragment thereof may be obtained from microorganisms by genetic recombination technologies or commercially available, without being limited thereto.

As used herein, the term "homology" refers to the degree of similarity between amino acid sequences of a wild-type protein or nucleotide sequences encoding the same and includes a sequence identical to the amino acid sequence or nucleotide sequence of the present invention by the above-described percentage or more. The homology may be determined by comparing the sequences via visual observation but may also be determined using a bioinformatic algorithm, which provides analysis results of a degree of homology by aligning sequences to be compared. The homology between the two amino acid sequences may be indicated in percentage. Useful automated algorithms may be used in GAP, BESTFIT, FASTA, and TFASTA computer software modules of Wisconsin Genetics Software Package (Genetics Computer Group, Madison, Wis., USA). The automated alignment algorithms in the modules include the Needleman & Wunsch algorithm, the Pearson & Lipman algorithm, and the Smith & Waterman sequence algorithm. Other useful algorithms and homology determinations on alignment are automated in software such as FASTP, BLAST, BLAST2, PSIBLAST, and CLUSTAL W.

Information on sequences of the physiologically active polypeptide, and the variant, derivative, and fragment thereof, and nucleotide sequences encoding the same may be obtained from known database of the NCBI GenBank, or the like.

The amino acids substituted or added may be not only 20 amino acids commonly found in human proteins but also atypical or non-naturally occurring amino acids. Commercial sources of atypical amino acids may include Sigma-Aldrich, ChemPep Inc. and Genzyme pharmaceuticals. The peptides including theses amino acids and typical peptide sequences may be synthesized and purchased from commercial suppliers, e.g., American Peptide Company, Bachem (USA) or Anygen (Korea).

In addition, the physiologically active polypeptide, and the variant, derivative, and fragment thereof according to the present invention may be in a varied form where the N-terminus and/or C-terminus is chemically modified or protected by organic groups, or amino acids may be added to the termini of the peptide, for protection from proteases in vivo while increasing stability thereof.

Particularly, since the N- and C-termini of chemically-synthesized peptides are electrically charged, the N-terminus may be acetylated and/or the C-terminus may be amidated to remove the charges, but the embodiment is not limited thereto.

In addition, the peptide according to the present invention includes all of those in the form of the peptide itself, a salt thereof (e.g., a pharmaceutically acceptable salt of the peptide), or a solvate thereof. Also, the peptide may be in any pharmaceutically acceptable form.

The type of the salt is not particularly limited. However, the salt is preferably in a form safe and effective to an individual, e.g., a mammal, without being limited thereto.

As used herein, the term "solvate" refers to a complex of the peptide or a salt thereof according to the present invention and a solvent molecule.

Although described as a "peptide consisting of a particular SEQ ID NO" in the present invention, it does not exclude a mutation that may occur naturally or by addition of a meaningless sequence upstream or downstream of the amino acid sequence of the SEQ ID NO, or a silent mutation thereof, as long as the peptide has activity identical or equivalent to that of the peptide consisting of the amino acid sequence, and even when such sequence addition or mutation is present, it obviously belongs to the scope of the present invention.

The method for preparing the long-acting drug conjugate according to the present invention may be a method for preparing a conjugate in which a physiologically active polypeptide is linked to an immunoglobulin Fc region via a linker, without being limited thereto.

In the present invention, linkage between the linker and the immunoglobulin Fc region may be formed by a covalent bond or a non-covalent bond between one end of the linker and the N-terminus of the immunoglobulin Fc region, but binding sites or methods for the linkage are not particularly limited. Specifically, the mono-PEGylated immunoglobulin Fc region may be prepared by linking a proline at the N-terminus of the immunoglobulin Fc region to a —CHO group of the linker, without being limited thereto.

In the present invention, the linker may have a structure of Formula 4 below, but is not limited thereto:

[Formula 4]

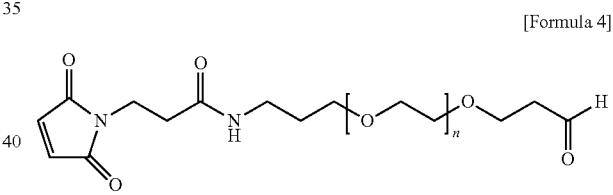

In Formula 4 above, n is from 200 to 250.

In addition, the linker may have a size of 1 kDa to 200 kDa, 1 kDa to 150 kDa, 1 kDa to 100 kDa, 1 kDa to 50 kDa, or 1 kDa to 10 kDa, without being limited thereto.

The mono-PEGylated immunoglobulin Fc region may have a structure of Formula 2 below, without being limited thereto.

[Formula 2]

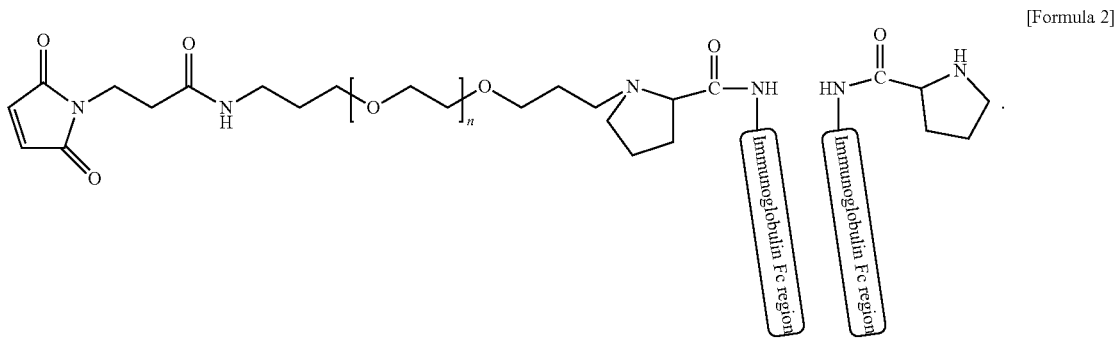

The preparation method of the present invention may be performed by linking the physiologically active polypeptide to one end of the mono-PEGylated immunoglobulin Fc region having the structure of Formula 2, without being limited thereto.

In addition, the other end of the linker which is not linked to the immunoglobulin Fc region may be linked to the physiologically active polypeptide, specifically, a —SH group or an amino acid containing a —SH group, or a cysteine of the physiologically active polypeptide, without being limited thereto.

In the present invention, the long-acting drug conjugate may have a structure of Formula 5 below, without being limited thereto.

[Formula 5]

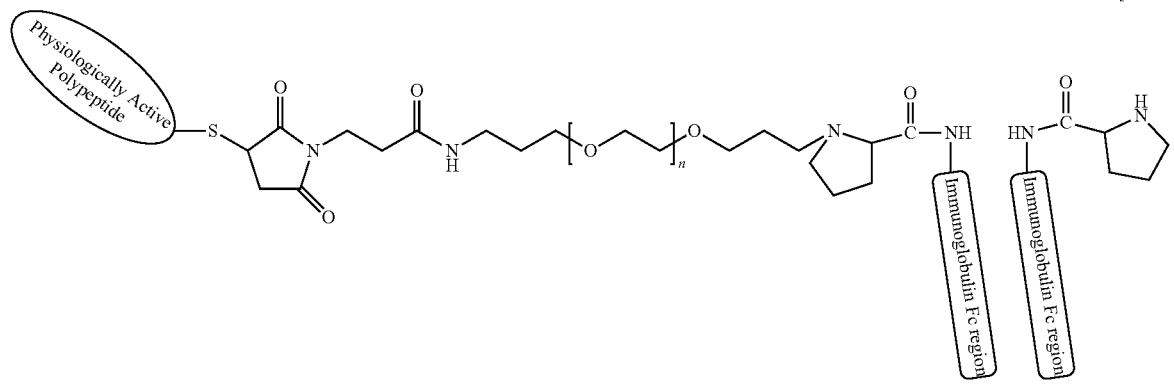

Formula 5 shows a structure in which the physiologically active polypeptide, the linker, and the immunoglobulin Fc region are sequentially linked from the left, without being limited thereto.

When the long-acting drug conjugate is prepared according to the preparation method of the present invention in which the mono-PEGylated immunoglobulin Fc region is prepared first and linked to the physiologically active polypeptide, it was confirmed that the purity of the final conjugate may be maintained with an increased yield compared to the conventional preparation method although the ultrafiltration/diafiltration and hydrophobic interaction chromatography processes are omitted and only the final purification process (e.g., one cycle of hydrophobic interaction chromatography) is performed in the preparation method according to the present invention.

Another aspect of the present invention provides a long-acting drug conjugate prepared by the above-described method.

Because the long-acting drug conjugate prepared by the preparation of the present invention has an increased half-life compared to the physiologically active polypeptide that is not linked to the linker or the immunoglobulin Fc region, advantageous effects on preparation of drugs may be obtained.

The long-acting drug conjugate prepared by the preparation method of the present invention may be used in preparation of drugs or compositions for the purposes of prevention, treatment, and alleviation of diseases.

Hereinafter, the present invention will be described in more detail with reference to the following examples. However, the following examples are merely presented to exemplify the present invention, and the scope of the present invention is not limited thereto.

Comparative Example: Preparation of Conjugate by Linking PEGylated Physiologically Active Polypeptide to Immunoglobulin Fc Region A PEGylated physiologically active polypeptide was linked to an immunoglobulin Fc region to prepare a long-acting conjugate.

Comparative Example 1: Preparation of Conjugate by Linking PEGylated GLP-1/GIP/Glucagon Trigonal Agonist Analog 1 to Immunoglobulin Fc Region In order to PEGylate a physiologically active polypeptide (GLP-1/GIP/Glucagon trigonal agonist analog 1, SEQ ID NO: 1) at a cysteine residue (—SH group), the GLP-1/GIP/Glucagon trigonal agonist analog 1 was reacted with a linker containing PEG (maleimide-10 kDa-PEG-aldehyde) (Formula 4) for about 1 hour in a molar ratio of 1:1.0 to 1:1.3 with a GLP-1/GIP/Glucagon trigonal agonist analog 1 concentration of about 3 g/L. Specifically, the reaction was performed in a 50 mM Tris buffer containing isopropanol (pH of 7.5, 6° C.±4° C.). In order to obtain a mono-PEGylated GLP-1/GIP/Glucagon trigonal agonist analog 1, the reaction solution was diluted with an equilibrium buffer including sodium citrate and ethanol to a total volume of 20 times and purified. In this regard, the mono-PEGylated GLP-1/GIP/Glucagon trigonal agonist analog 1 was purified using an SP High Performance column (GE Healthcare, cation-exchange chromatography) using a solution including sodium citrate and ethanol and a potassium chloride concentration gradient. After the purified solution of the PEGylated GLP-1/GIP/Glucagon trigonal agonist analog 1 was diluted with water, the buffer solution was replaced with a 0.1 M potassium phosphate solution through ultrafiltration/diafiltration (UF/DF), followed by concentration to recover a resultant with a final concentration of about 3 g/L or more.

The mono-PEGylated GLP-1/GIP/Glucagon trigonal agonist analog 1 prepared as described above was linked to an immunoglobulin Fc region to prepare a long-acting conjugate as follows.

In order to link an aldehyde group of PEG of the mono-PEGylated GLP-1/GIP/Glucagon trigonal agonist analog 1 to the amino terminus of an immunoglobulin Fc region, the mono-PEGylated GLP-1/GIP/Glucagon trigonal agonist analog 1 was reacted with the immunoglobulin Fc region in a molar ratio of 1:2 at a temperature of 6° C.±4° C. for about 12 hours with a total protein concentration (GLP-1/GIP/Glucagon trigonal agonist analog 1 and immunoglobulin Fc region) of 30 g/L.

In order to isolate and remove unreacted immunoglobulin Fc regions after the reaction for linkage, the reaction solution was purified using a Butyl 4 Fast Flow column (GE Healthcare, hydrophobic interaction chromatography). In this case, a Tris buffer and sodium chloride were added to the reaction solution, and the reaction solution was purified using a solution including a Bis-Tris and a sodium chloride concentration gradient.

Thereafter, using a Source 15ISO column (GE Healthcare), hydrophobic interaction chromatography was performed. By-products were eliminated by this process, and an immunoglobulin Fc region-PEG-containing linker-GLP-1/GIP/Glucagon trigonal agonist analog 1 conjugate was obtained. In this case, purification was performed using a buffer including sodium citrate and an ammonium sulfate concentration gradient.

Comparative Example 2: Preparation of Conjugate by Linking PEGylated Glucagon Analog 1 to Immunoglobulin Fc Region In order to PEGylate a physiologically active polypeptide (Glucagon analog 1, SEQ ID NO: 4) at a cysteine residue (—SH group), Glucagon analog 1 was reacted with a linker containing PEG (maleimide-10 kDa-PEG-aldehyde) (Formula 1) for about 1 hour in a molar ratio of 1:1.3 with a Glucagon analog 1 concentration of 3 g/L. Specifically, the reaction was performed in a 50 mM Tris buffer containing isopropanol (pH of 7.3). In order to obtain a mono-PEGylated Glucagon analog 1, the reaction solution was diluted with an equilibrium buffer including sodium citrate and ethanol to a total volume of 20 times and purified. In this regard, the mono-PEGylated Glucagon analog 1 was purified using an SP High Performance column (GE Healthcare, cation-exchange chromatography) using a solution including sodium citrate and ethanol and a potassium chloride concentration gradient. After the purified solution of the PEGylated Glucagon analog 1 was diluted with water, the buffer solution was replaced with a 0.1 M potassium phosphate solution through ultrafiltration/diafiltration (UF/DF), followed by concentration to recover a resultant with a final concentration of 3 g/L or more.

The mono-PEGylated Glucagon analog 1 prepared as described above was linked to an immunoglobulin Fc region to prepare a long-acting conjugate as follows.

In order to link an aldehyde group of PEG of the mono-PEGylated Glucagon analog 1 to the amino terminus of the immunoglobulin Fc region, the mono-PEGylated Glucagon analog 1 was reacted with the immunoglobulin Fc region in a molar ratio of 1:5 at a temperature of 6° C.±4° C. for about 12 hours with a total protein concentration (Glucagon analog 1 and immunoglobulin Fc region) of 20 g/L.

In order to isolate and remove unreacted immunoglobulin Fc regions after the reaction for linkage, the reaction solution was purified using a Butyl 4 Fast Flow column (GE Healthcare, hydrophobic interaction chromatography). In this case, a Tris buffer and sodium chloride were added to the reaction solution, and the reaction solution was purified using a solution including Bis-Tris and a sodium chloride concentration gradient.

Thereafter, using a Source 15ISO column (GE Healthcare), hydrophobic interaction chromatography was performed. By-products were eliminated by this process, and an immunoglobulin Fc region-PEG-containing linker-Glucagon analog 1 conjugate was obtained. In this case, purification was performed using a buffer including sodium citrate and an ammonium sulfate concentration gradient.

The present inventors have developed a process capable of efficiently producing the conjugate with a high purity by omitting the membrane filtration process and the purification process (hydrophobic interaction chromatography, Butyl 4 Fast Flow) from the process of preparing the conjugate according to the above-described Comparative Examples 1 and 2 as follows.

Example 1: Preparation of Mono-PEGylated Immunoglobulin Fc Region

Example 1-1. Preparation of Mono-PEGylated Immunoglobulin Fc Region

In order to PEGylate the N-terminus of an immunoglobulin Fc region (49.8 kDa) having a hinge region with a Pro-Ser-Cys-Pro (SEQ ID NO: 9) sequence at the N-terminus, the immunoglobulin Fc region was reacted with a linker containing PEG (structure of Formula 4, 10 kDa) in a molar ratio (immunoglobulin Fc region: PEG-containing linker) of 1:1 with an immunoglobulin Fc region concentration of 50 g/L at 6° C.±4° C. for about 4 hours.

[Formula 4]

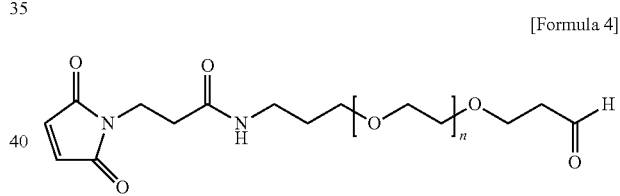

Specifically, the reaction was performed in a composition including a 5 mM Bis-Tris buffer (pH 6.5) and potassium phosphate, and 10 mM NaCNBH$_3$ (sodium cyanoborohydride) was added thereto as a reducing agent. In order to obtain a mono-PEGylated immunoglobulin Fc region, the reaction solution was diluted with the Bis-Tris buffer and purified.

Unlike the preparation method of the above-described Comparative Examples in which the mono-PEGylated GLP-1/GIP/Glucagon trigonal agonist analog and glucagon analog were purified by cation-exchange chromatography, the mono-PEGylated immunoglobulin Fc region was purified using a CaptoQ ImpRes column (GE Healthcare, anion-exchange chromatography) using a Bis-Tris buffer and a sodium chloride concentration gradient.

Example 1-2. Analysis of Structure of Mono-PEGylated Immunoglobulin Fc Region

The mono-PEGylated immunoglobulin Fc region prepared in Example 1-1 was structurally analyzed by MALDI-TOF and Peptide mapping. As a result of MALDI-TOF, the resultant was identical to an expected molecular weight of the mono-PEGylated immunoglobulin Fc region (FIG. 1), and as a result of Peptide mapping, it was confirmed that over 90% of PEG was PEGylated at the N-terminus of the immunoglobulin Fc region.

Meanwhile, as a result of analyzing the mono-PEGylated immunoglobulin Fc region (Formula 2) prepared in Example 1-1 above using SE-HPLC, RP-HPLC, and IE-HPLC assays, the purity was confirmed to be 90% or more in SE-HPLC, 90% or more in RP-HPLC, and 80% or more in IE-HPLC.

globulin Fc region to the GLP-1/GIP/Glucagon trigonal agonist analog 1, the mono-PEGylated immunoglobulin Fc region was reacted with the GLP-1/GIP/Glucagon trigonal agonist analog 1 in a molar ratio of 1:1 with a GLP-1/GIP/Glucagon trigonal agonist analog 1 concentration of 0.2 g/L at 6° C.±4° C. for about 2 hours. The reaction was performed in a Tris-Cl buffer (6° C.±4° C.) including isopropanol. As a result of analyzing the resultant after reaction using SE-HPLC, RP-HPLC, and IE-HPLC assays, the purity was

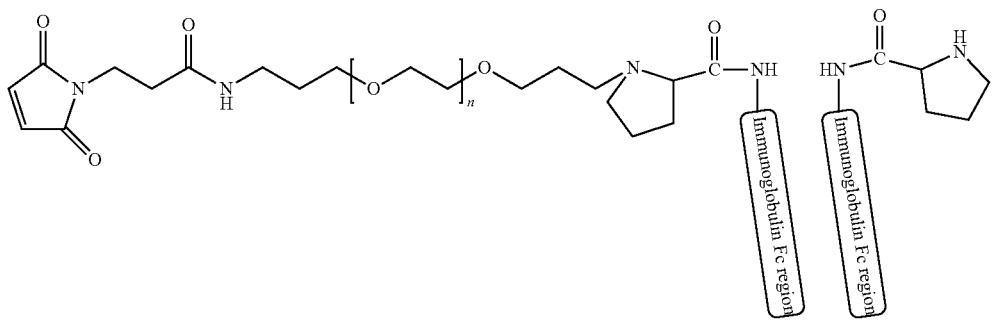

[Formula 2]

Example 2: Preparation of Conjugate by Linking PEGylated Immunoglobulin Fc Region to Physiologically Active Polypeptide Long-acting conjugates were prepared as follows by linking the mono-PEGylated immunoglobulin Fc region prepared in Example 1-1 to various physiologically active peptides.

Unlike the preparation method of the Comparative Examples where the PEGylated physiologically active polypeptide was purified by cation-exchange chromatography and then subjected to buffer exchange and concentration by ultrafiltration/diafiltration (UF/DF), the mono-PEGylated immunoglobulin Fc region was reacted with the physiologically active polypeptide via peptide conjugation without performing ultrafiltration/diafiltration. Long-acting conjugates prepared as described above had high purity, and thus one of the two cycles of hydrophobic interaction chromatography could be omitted unlike the preparation method according to the Comparative Examples.

Example 2-1. Preparation of Conjugate of GLP-1/GIP/Glucagon Trigonal Agonist Analog 1

A long-acting conjugate (immunoglobulin Fc region-PEG-containing linker-GLP-1/GIP/Glucagon trigonal agonist analog 1) was prepared via peptide conjugation of the GLP-1/GIP/Glucagon trigonal agonist analog 1 (SEQ ID NO: 1), after anion-exchange chromatography of Example 1-1, without performing ultrafiltration/diafiltration.

confirmed to be 90% or more in SE-HPLC, 80% or more in RP-HPLC, and 70% or more in IE-HPLC.

Thereafter, the resultant of the reaction was subjected to hydrophobic interaction chromatography once using a Source 15ISO column (GE Healthcare). By-products were eliminated by this process, and an immunoglobulin Fc region-PEG-containing linker-GLP-1/GIP/Glucagon trigonal agonist analog 1 conjugate was obtained. In this case, purification was performed using a buffer including sodium citrate and an ammonium sulfate concentration gradient. It was confirmed that a yield obtained herein was increased by about twice or more compared to a yield of Comparative Example 1 with the same amount of the GLP-1/GIP/Glucagon trigonal agonist analog 1.

The eluted immunoglobulin Fc region-PEG-containing linker-GLP-1/GIP/Glucagon trigonal agonist analog 1 conjugate was analyzed by SE-HPLC, RP-HPLC, and IE-HPLC assays, and high purity was confirmed since the purity was 90% or more in SE-HPLC, 90% or more in RP-HPLC, and 90% or more in IE-HPLC.

Example 2-2. Preparation of Conjugate of GLP-1/GIP/Glucagon Trigonal Agonist Analog 2

A long-acting conjugate (immunoglobulin Fc region-PEG-containing linker-GLP-1/GIP/Glucagon trigonal agonist analog 2) was prepared via peptide conjugation of the GLP-1/GIP/Glucagon trigonal agonist analog 2 (SEQ ID NO: 2), after anion-exchange chromatography of Example 1-1, without performing ultrafiltration/diafiltration.

[SEQ ID NO: 1]
Y-Aib-QGT FTSDY SKYLD EKRAK EFVQW LLDHH PSSGQ PPPSC

Aib = 2-aminoisobutyric acid
Glu16 and Lys20 linked by Lactam ring

[SEQ ID NO: 2]
YXQGTFTSDYSKYLDEKRAKEFVQWLLDHHCSSGQPPPS

Glu16 and Lys20 linked by Lactam ring

In this regard, in order to link a maleimide reactive group at one terminus of PEG of the mono-PEGylated immuno- In this regard, in order to link a maleimide reactive group at one terminus of PEG of the mono-PEGylated immunoglobulin Fc region to the GLP-1/GIP/Glucagon trigonal agonist analog 2, the mono-PEGylated immunoglobulin Fc region was reacted with the GLP-1/GIP/Glucagon trigonal agonist analog 2 in a molar ratio of 1:1 with a GLP-1/GIP/Glucagon trigonal agonist analog 2 concentration of 0.2 g/L at 6° C.±4° C. for about 2 hours. The reaction was performed in a Tris-Cl buffer (6° C.±4° C.) including isopropanol. As a result of analyzing the resultant after reaction using SE-HPLC, RP-HPLC, and IE-HPLC assays, the purity of the long-acting conjugate including the GLP-1/GIP/Glucagon trigonal agonist analog 2 was confirmed to be 90% or more in SE-HPLC, 80% or more in RP-HPLC, and 70% or more in IE-HPLC.

Thereafter, the resultant of the reaction was subjected to hydrophobic interaction chromatography once using a Source 15ISO column (GE Healthcare). By-products were eliminated by this process, and an immunoglobulin Fc region-PEG-containing linker-GLP-1/GIP/Glucagon trigonal agonist analog 2 conjugate was obtained. In this case, purification was performed using a buffer including sodium citrate and an ammonium sulfate concentration gradient. It was confirmed that a yield obtained herein was increased by about twice or more compared to a yield of Comparative Example 1 with the same amount of the GLP-1/GIP/Glucagon trigonal agonist analog 2.

The eluted immunoglobulin Fc region-PEG-containing linker-GLP-1/GIP/Glucagon trigonal agonist analog 2 conjugate was analyzed by SE-HPLC, RP-HPLC, and IE-HPLC assays, and high purity was confirmed since the purity was 90% or more in SE-HPLC, 90% or more in RP-HPLC, and 80% or more in IE-HPLC.

Example 2-3. Preparation of Conjugate of GLP-1/GIP/Glucagon Trigonal Agonist Analog 3

A long-acting conjugate (immunoglobulin Fc region-PEG-containing linker-GLP-1/GIP/Glucagon trigonal agonist analog 3) was prepared via peptide conjugation of the GLP-1/GIP/Glucagon trigonal agonist analog 3 (SEQ ID NO: 3), after anion-exchange chromatography of Example 1-1, without performing ultrafiltration/diafiltration.

[SEQ ID NO: 3]

HXQGTFTSDYSKYLDEKRAKEFVQWLLDHHPSSGQPPPSC
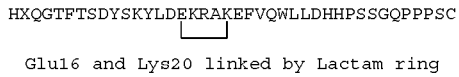

Glu16 and Lys20 linked by Lactam ring

In this regard, in order to link a maleimide reactive group at one terminus of PEG of the mono-PEGylated immunoglobulin Fc region to cysteine of the GLP-1/GIP/Glucagon trigonal agonist analog 3, the mono-PEGylated immunoglobulin Fc region was reacted with the GLP-1/GIP/Glucagon trigonal agonist analog 3 in a molar ratio of 1:1 with a GLP-1/GIP/Glucagon trigonal agonist analog 3 concentration of 0.2 g/L at 6° C.±4° C. for about 2 hours. The reaction was performed in a Tris-Cl buffer (6° C.±4° C.) including isopropanol. As a result of analyzing the resultant after reaction using SE-HPLC, RP-HPLC, and IE-HPLC assays, the purity was confirmed to be 90% or more in SE-HPLC, 80% or more in RP-HPLC, and 70% or more in IE-HPLC.

Thereafter, the resultant of the reaction was subjected to hydrophobic interaction chromatography once using a Source 15ISO column (GE Healthcare). By-products were eliminated by this process, and an immunoglobulin Fc region-PEG-containing linker-GLP-1/GIP/Glucagon trigonal agonist analog 3 conjugate was obtained. In this case, purification was performed using a buffer including sodium citrate and an ammonium sulfate concentration gradient. It was confirmed that a yield obtained herein was increased by about twice or more compared to a yield of Comparative Example 1 with the same amount of the GLP-1/GIP/Glucagon trigonal agonist analog 3.

The eluted immunoglobulin Fc region-PEG-containing linker-GLP-1/GIP/Glucagon trigonal agonist analog 3 conjugate was analyzed by SE-HPLC, RP-HPLC, and IE-HPLC assays, and high purity was confirmed since the purity was 90% or more in SE-HPLC, 90% or more in RP-HPLC, and 90% or more in IE-HPLC.

Example 2-4. Preparation of Conjugate of Glucagon Analog 1

A long-acting conjugate (immunoglobulin Fc region-PEG-containing linker-Glucagon analog 1) was prepared via peptide conjugation of Glucagon analog 1 (SEQ ID NO: 4), after anion-exchange chromatography of Example 1-1, without performing ultrafiltration/diafiltration.

[SEQ ID NO: 4]

Y-Aib-QGTFTSDY$_{10}$SKYLDEKRAK$_{20}$EFVQWLMNTC$_{30}$

Aib = 2-aminoisobutyric acid
Glu16 and Lys20 linked by Lactam ring

In this regard, in order to link a maleimide reactive group at one terminus of PEG of the mono-PEGylated immunoglobulin Fc region to Glucagon analog 1, the mono-PEGylated immunoglobulin Fc region was reacted with Glucagon analog 1 in a molar ratio of 1:1 with a Glucagon analog 1 concentration of 0.2 g/L at 6° C.±4° C. for about 2 hours. The reaction was performed in a Tris-Cl buffer (6° C.±4° C.) including isopropanol. As a result of analyzing the resultant after reaction using SE-HPLC, RP-HPLC, and IE-HPLC assays, the purity of the immunoglobulin Fc region-PEG-containing linker-Glucagon analog 1 was confirmed to be 90% or more in SE-HPLC, 70% or more in RP-HPLC, and 70% or more in IE-HPLC.

Thereafter, the resultant of the reaction was subjected to hydrophobic interaction chromatography once using a Source 15ISO column (GE Healthcare). By-products were eliminated by this process, and an immunoglobulin Fc region-PEG-containing linker-Glucagon analog 1 conjugate was obtained. In this case, purification was performed using a buffer including sodium citrate and an ammonium sulfate concentration gradient. It was confirmed that a yield obtained herein was increased by about 1.5 times or more compared to a yield of Comparative Example 2 with the same amount of Glucagon analog 1.

The eluted immunoglobulin Fc region-PEG-containing linker-Glucagon analog 1 conjugate was analyzed by SE-HPLC, RP-HPLC, and IE-HPLC assays, and high purity was confirmed since the purity was 90% or more in SE-HPLC, 90% or more in RP-HPLC, and 90% or more in IE-HPLC.

Example 2-5. Preparation of Conjugate of Glucagon Analog 2

A long-acting conjugate (immunoglobulin Fc region-PEG-containing linker-Glucagon analog 2) was prepared via peptide conjugation of Glucagon analog 2 (SEQ ID NO: 5), after anion-exchange chromatography of Example 1-1, without performing ultrafiltration/diafiltration.

[SEQ ID NO: 5]

YXQGTFTSDYSKYLDECRAKEFVQWLMNT

Glu16 and Lys20 linked by Lactam ring

In this regard, in order to link a maleimide reactive group at one terminus of PEG of the mono-PEGylated immunoglobulin Fc region to Glucagon analog 2, the mono-PEGylated immunoglobulin Fc region was reacted with Glucagon analog 2 in a molar ratio of 1:1 with a Glucagon analog 2 concentration of 0.2 g/L at 6° C.±4° C. for about 2 hours. The reaction was performed in a Tris-Cl buffer (6° C.±4° C.) including isopropanol. As a result of analyzing the resultant after reaction using SE-HPLC, RP-HPLC, and IE-HPLC assays, the purity of the immunoglobulin Fc region-PEG-containing linker-Glucagon analog 2 was confirmed to be 90% or more in SE-HPLC, 70% or more in RP-HPLC, and 70% or more in IE-HPLC.

Thereafter, the resultant of the reaction was subjected to hydrophobic interaction chromatography once using a Source 15ISO column (GE Healthcare). By-products were eliminated by this process, and an immunoglobulin Fc region-PEG-containing linker-Glucagon analog 2 conjugate was obtained. In this case, purification was performed using a buffer including sodium citrate and an ammonium sulfate concentration gradient. It was confirmed that a yield obtained herein was increased by about 1.5 times or more compared to a yield of Comparative Example 2 with the same amount of Glucagon analog 2.

The eluted immunoglobulin Fc region-PEG-containing linker-Glucagon analog 2 conjugate was analyzed by SE-HPLC, RP-HPLC, and IE-HPLC assays, and high purity was confirmed since the purity was 90% or more in SE-HPLC, 90% or more in RP-HPLC, and 90% or more in IE-HPLC.

Example 2-6. Preparation of Conjugate of Glucagon Analog 3

A long-acting conjugate (immunoglobulin Fc region-PEG-containing linker-Glucagon analog 3) was prepared via peptide conjugation of Glucagon analog 3 (SEQ ID NO: 6), after anion-exchange chromatography of Example 1-1, without performing ultrafiltration/diafiltration.

[SEQ ID NO: 6]

YXQGTFTSDYSKYLDSRRAQDFVQWLMNTC

In this regard, in order to link a maleimide reactive group at one terminus of PEG of the mono-PEGylated immunoglobulin Fc region to cysteine of Glucagon analog 3, the mono-PEGylated immunoglobulin Fc region was reacted with Glucagon analog 3 in a molar ratio of 1:1 with a Glucagon analog 3 concentration of 0.2 g/L at 6° C.±4° C. for about 2 hours. The reaction was performed in a Tris-Cl buffer (6° C.±4° C.) including isopropanol. As a result of analyzing the resultant after reaction using SE-HPLC, RP-HPLC, and IE-HPLC assays, the purity of the immunoglobulin Fc region-PEG-containing linker-Glucagon analog 3 was confirmed to be 90% or more in SE-HPLC, 70% or more in RP-HPLC, and 70% or more in IE-HPLC.

Thereafter, the resultant of the reaction was subjected to hydrophobic interaction chromatography once using a Source 15ISO column (GE Healthcare). By-products were eliminated by this process, and an immunoglobulin Fc region-PEG-containing linker-Glucagon analog 3 conjugate was obtained. In this case, purification was performed using a buffer including sodium citrate and an ammonium sulfate concentration gradient. It was confirmed that a yield obtained herein was increased by about 1.5 times or more compared to the existing yield with the same amount of Glucagon analog 3.

The eluted immunoglobulin Fc region-PEG-containing linker-Glucagon analog 3 conjugate was analyzed by SE-HPLC, RP-HPLC, and IE-HPLC assays, and high purity was confirmed since the purity was 90% or more in SE-HPLC, 90% or more in RP-HPLC, and 90% or more in IE-HPLC.

Tables 1 and 2 show comparison results between the methods the comparative examples and examples.

TABLE 1

| | COMPARISON BETWEEN PREPARATION METHODS OF GLP-1/GIP/Glucagon TRIGONAL AGONIST ANALOG | | | |
|---|---|---|---|---|
| | COMPARATIVE EXAMPLE | EXAMPLE (CONVENTIONAL PREPARATION METHOD) | | |
| | GLP-1/GIP/Glucagon TRIGOAL AGONIST ANALOG 1 | GLP-1/GIP/Glucagon TRIGOAL AGONIST ANALOG 1 | GLP-1/GIP/Glucagon TRIGOAL AGONIST ANALOG 2 | GLP-1/GIP/Glucagon TRIGOAL AGONIST ANALOG 3 |
| REACTION CONDITIONS | REACTION 1] Peptide:PEG = 1:1.3 REACTION 2] PEG-Peptide:IMMUNOGLOBULIN Fc REGION = 1:2 | REACTION 1] Fc:PEG = 1:1 REACTION 2] PEG-Fc:Peptide = 1:1 | | |
| | PURITY | | | |
| SE-HPLC | 90% OR MORE | 90% OR MORE | 90% OR MORE | 90% OR MORE |
| RP-HPLC | 90% OR MORE | 90% OR MORE | 90% OR MORE | 90% OR MORE |
| IE-HPLC | 90% OR MORE | 90% OR MORE | 80% OR MORE | 90% OR MORE |
| YIELD (WITH RESPECT TO PEPTIDE) | — | TWICE OR MORE HIGHER THAN COMPARATIVE EXAMPLE | TWICE OR MORE HIGHER THAN COMPARATIVE EXAMPLE | TWICE OR MORE HIGHER THAN COMPARATIVE EXAMPLE |

TABLE 1-continued

COMPARISON BETWEEN PREPARATION METHODS OF GLP-1/GIP/Glucagon TRIGONAL AGONIST ANALOG

|  | COMPARATIVE EXAMPLE | EXAMPLE (CONVENTIONAL PREPARATION METHOD) | | |
| --- | --- | --- | --- | --- |
|  | GLP-1/GIP/Glucagon TRIGOAL AGONIST ANALOG 1 | GLP-1/GIP/Glucagon TRIGOAL AGONIST ANALOG 1 | GLP-1/GIP/Glucagon TRIGOAL AGONIST ANALOG 2 | GLP-1/GIP/Glucagon TRIGOAL AGONIST ANALOG 3 |
| YIELD (WITH RESPECT TO Fc) |  | ABOUT 1.3 TIMES HIGHER THAN COMPARATIVE EXAMPLE | ABOUT 1.3 TIMES HIGHER THAN COMPARATIVE EXAMPLE | ABOUT 1.3 TIMES HIGHER THAN COMPARATIVE EXAMPLE |

TABLE 2

COMPARISON BETWEEN METHODS FOR PREPARING GLUCAGON ANALOGS

|  | COMPARATIVE EXAMPLE (CONVENTIONAL PREPARATION METHOD) | EXAMPLE (REVERSE ORDER PREPARATION METHOD) | | |
| --- | --- | --- | --- | --- |
|  | GLUCAGON ANALOG 1 | GLUCAGON ANALOG 1 | GLUCAGON ANALOG 2 | GLUCAGON ANALOG 3 |
| REACTION CONDITIONS | REACTION 1] Peptide:PEG = 1:1.3 REACTION 2] PEG-Peptide:IMMUNOGLOBULIN Fc REGION = 1:5 | REACTION 1] Fc:PEG = 1:1 REACTION 2] PEG-Fc:Peptide = 1:1 | | |
|  | PURITY | | | |
| SE-HPLC | 90% OR MORE | 90% OR MORE | 90% OR MORE | 90% OR MORE |
| RP-HPLC | 90% OR MORE | 90% OR MORE | 90% OR MORE | 90% OR MORE |
| IE-HPLC | 90% OR MORE | 90% OR MORE | 90% OR MORE | 90% OR MORE |
| YIELD (WITH RESPECT TO PEPTIDE) | — | 1.5 TIMES OR MORE HIGHER THAN COMPARATIVE EXAMPLE | 1.5 TIMES OR MORE HIGHER THAN COMPARATIVE EXAMPLE | 1.5 TIMES OR MORE HIGHER THAN COMPARATIVE EXAMPLE |
| YIELD (WITH RESPECT TO Fc) |  | TIMES OR MORE HIGHER THAN COMPARATIVE EXAMPLE | TIMES OR MORE HIGHER THAN COMPARATIVE EXAMPLE | TIMES OR MORE HIGHER THAN COMPARATIVE EXAMPLE |

The above description of the present invention is provided for the purpose of illustration, and it would be understood by those skilled in the art that various changes and modifications may be made without changing technical conception and essential features of the present invention. Thus, it is clear that the above-described embodiments are illustrative in all aspects and do not limit the present invention. Therefore, the scope of the disclosure is defined not by the detailed description, but by the claims and their equivalents, and all variations within the scope of the claims and their equivalents are to be construed as being included in the disclosure.

The invention claimed is:

1. A compound having a structure of Formula 2 below or a stereoisomer, a solvate, or a pharmaceutically acceptable salt thereof:

Formula 2

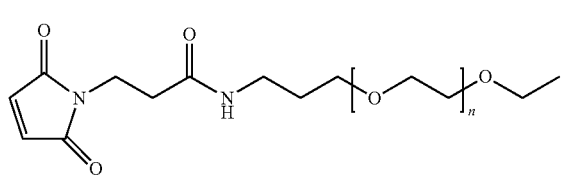

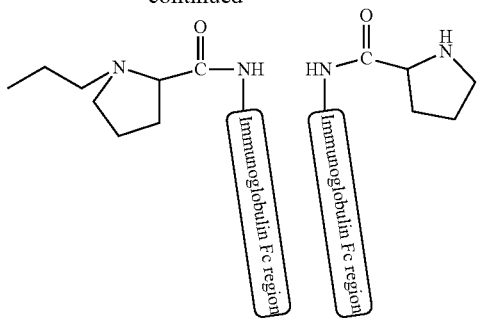

wherein in Formula 2 above, n is from 200 to 250.

2. A composition for preparing a long-acting drug conjugate compound having a structure of Formula 2 below or a stereoisomer, a solvate, or a pharmaceutically acceptable salt thereof, wherein the drug is a physiologically active polypeptide:

Formula 2

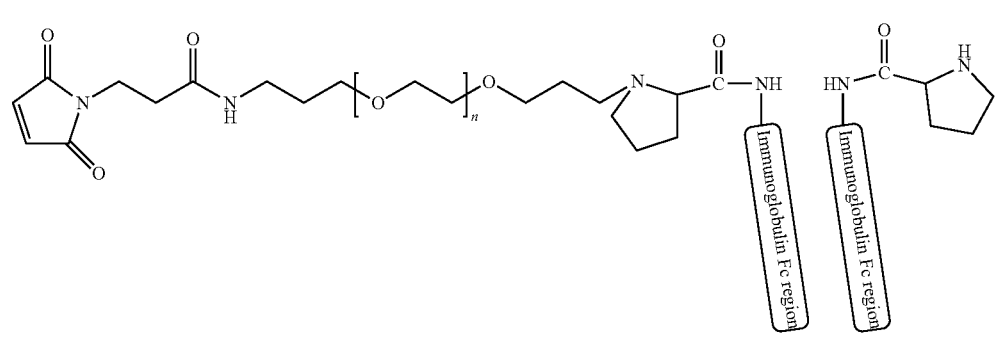

wherein in Formula 2 above, n is from 200 to 250.

3. A long-acting drug conjugate prepared by reacting the composition of claim 2 with a physiologically active polypeptide.

4. A method for preparing a long-acting conjugate of a physiologically active polypeptide, the method comprising:
preparing a conjugate by linking a compound having a structure of Formula 2 below or a stereoisomer, a solvate, or a pharmaceutically acceptable salt thereof, to a physiologically active polypeptide:

Formula 2

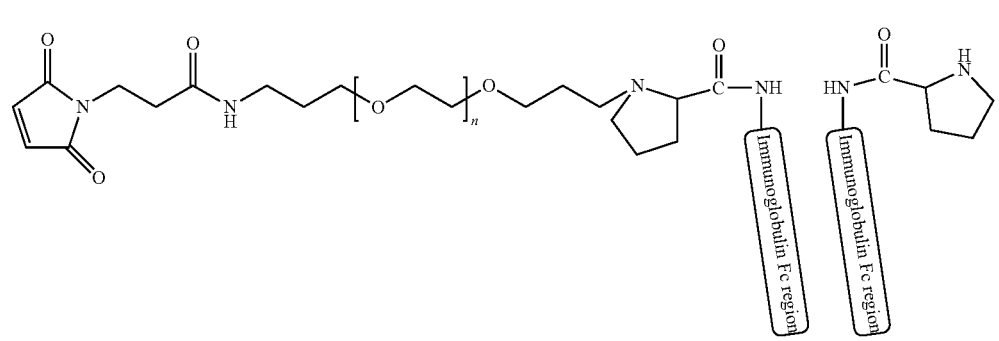

wherein in Formula 2 above, n is from 200 to 250.

5. A long-acting drug conjugate prepared by the method of claim 4.

* * * * *